US008449864B2

(12) United States Patent
Piliponsky et al.

(10) Patent No.: US 8,449,864 B2
(45) Date of Patent: May 28, 2013

(54) NEUROTENSIN AS A MARKER AND THERAPEUTIC TARGET FOR SEPSIS

(75) Inventors: Adrian Martin Piliponsky, Mountain View, CA (US); Mindy Tsai, Palo Alto, CA (US); Stephen J. Galli, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1270 days.

(21) Appl. No.: 11/875,710

(22) Filed: Oct. 19, 2007

(65) Prior Publication Data
US 2008/0213270 A1 Sep. 4, 2008

Related U.S. Application Data

(60) Provisional application No. 60/853,147, filed on Oct. 20, 2006.

(51) Int. Cl.
*A61B 5/145* (2006.01)
*G01N 33/49* (2006.01)
*C07K 16/00* (2006.01)

(52) U.S. Cl.
CPC ..................... *A61B 5/145* (2013.01)
USPC .......... 424/9.1; 435/7.1; 435/7.95; 530/387.1

(58) Field of Classification Search
None
See application file for complete search history.

(56) References Cited

U.S. PATENT DOCUMENTS
2006/0052278 A1* 3/2006 Powell .............................. 514/1

FOREIGN PATENT DOCUMENTS
WO WO2004059293 A2 7/2004

OTHER PUBLICATIONS

Hubbard et al., Cecal Ligation and Puncture, shock, 24(Suppl1):52-57, 2005.*
Cuber et al., Plasma Neurotensin in the Conscious Pig, Pancreas, 5(3):306-313, 1990.*
Wilding JPH, Neuropeptides and appetite control, Diabetes UK, Diabetic Medicine,19:619-627, 2002.*
Gaumann et al., "Adrenal and intestinal secretion of catecholamines and neuropeptides during splanchnic artery occlusion shock," Circ. Shock., 1988, 26(4):391-407.
Kawakami et al., "Regulation of mast-cell and basophil function and survival by IgE," Nat. Rev. Immunol., 2002, 2 (10):773-786.
Kempuraj et al., "Characterization of mast cell-committed progenitors present in human umbilical cord blood," Blood, 1999, 93(10):3338-3346.
Mai et al., "Neurotensin in the human brain," Neuroscience, 1987, 22(2):499-524.
Maurer et al., "Mast cells promote homeostasis by limiting endothelin-1-induced toxicity," Nature, 2004, 432 (7016):512-516.
Maurer et al., "The c-kit ligand, stem cell factor, can enhance innate immunity through effects on mast cells," J Exp. Med., 1998, 188(12):2343-2348.
O'Hara et al., "Consequences of Citrobacter rodentium infection on enteroendocrine cells and the enteric nervous system in the mouse colon," Cell Microbiol., 2006, 8(4):646-660.
Staub et al., "Campylobacter pylori colonization of the antrum: effect of gastrin, somatostatin, pancreatic polypeptide and neurotensin," Schweiz Med. Wochenschr., 1989, 119(21):765-767.
Svensson et al., "Neuromodulation of experimental Shigella infection reduces damage to the gut mucosa," Microbes Infect., 2004, 6(3):256-264.
Van Amersfoort et al., "Receptors, mediators, and mechanisms involved in bacterial sepsis and septic shock," Clin. Microbiol. Rev., 16(3):379-414, (2003).
Warkentin et al., "Platelet-endothelial interactions: sepsis, HIT, and antiphospholipid syndrome," Hematology Am. Soc. Hematol. Educ. Program., 2003, 2003(1):497-519.

* cited by examiner

*Primary Examiner* — Jeffrey Stucker
*Assistant Examiner* — Stacey N MacFarlane
(74) *Attorney, Agent, or Firm* — Bozicevic, Field & Francis LLP; Pamela J. Sherwood

(57) ABSTRACT

Sepsis is a complex, incompletely understood and often fatal disorder, typically accompanied by hypotension, that is considered to represent a dysregulated host response to an infection. Neurotensin (NT) is 13-amino-acid peptide that, among its multiple effects, induces hypotension. It is shown herein that plasma concentrations of NT are increased in humans with sepsis and in mice after caecal ligation and puncture (CLP), a model of sepsis. Mast cells can degrade NT through neurotensin receptor 1-and neurolysin-dependent mechanisms, diminishing the hypotensive effects of NT, reducing intraperitoneal NT concentrations, and improving survival. These findings show that mast cells can regulate NT concentrations, and identify NT as a biomarker and therapeutic target in sepsis.

3 Claims, 20 Drawing Sheets

NEUROTENSIN AS A MARKER AND THERAPEUTIC TARGET FOR SEPSIS

FEDERALLY-SPONSORED RESEARCH OR DEVELOPMENT

This invention was made with Government support under contracts A1023990, CA072074, and HL067674 awarded by the National Institutes of Health. The Government has certain rights in this invention.

BACKGROUND OF THE INVENTION

Methods that provide for early and accurate detection of disease conditions are of great interest for clinical practice, however certain conditions, including systemic inflammatory conditions, may reach an advanced state before diagnosis is possible. These conditions can result from an interaction between a pathogenic microorganism and the host's defense system, which triggers the host inflammatory response. The complexity of the host's response during the systemic inflammatory response has complicated efforts towards understanding disease pathogenesis.

Bacteremia and sepsis are closely related conditions. Bacteremia denotes bacteria in the bloodstream. Sepsis refers to a serious infection, localized, bacteremic or due to fungal infections, that is accompanied by systemic manifestations of inflammation. Septic shock is sepsis with hypoperfusion and hypotension refractory to fluid therapy. The more general term, systemic inflammatory response syndrome, recognizes that several severe conditions, including infections, pancreatitis, burns, trauma, etc. can trigger an acute inflammatory reaction, the systemic manifestations of which are associated with release into the bloodstream of a large number of endogenous mediators of inflammation.

Transient bacteremia may be caused by surgical manipulation of infected oral tissues or even routine dental manipulations; catheterization of an infected lower urinary tract; incision and drainage of an abscess; and colonization of indwelling devices, especially IV and intracardiac catheters, urethral catheters, and ostomy devices and tubes; and the like. Gram-negative bacteremia is typically intermittent and opportunistic; although it may have no effect on a healthy person, it can be seriously important in immunocompromised patients with debilitating underlying diseases, after chemotherapy, and in settings of malnutrition.

When bacteremia or infections with certain fungi produce changes in circulation such that tissue perfusion is critically reduced, septic shock ensues. Septic shock is most common with infections by gram-negative organisms, staphylococci, or meningococci. Septic shock is characterized by acute circulatory failure, usually with or followed by hypotension, and multiorgan failure.

The pathogenesis of septic shock is not completely understood. The bacterial toxins generated by the infecting organisms trigger complex immunologic reactions: a large number of mediators, including tumor necrosis factor, leukotrienes, lipoxygenase, histamine, bradykinin, serotonin, and interleukin-2, have been implicated in addition to endotoxin.

Initially, vasodilation of arteries and arterioles occurs. Later, cardiac output may decrease and peripheral resistance may increase. Decreased organ perfusion particularly affects the kidneys and brain, and subsequently causes failure of one or more of the visceral organs. Ultimately, cardiac output declines and the typical features of shock appear. At the onset of septic shock, the leukocyte count may be significantly reduced, and the polymorphonuclear leukocytes (PMNs) may be as low as 20%. However, this situation rapidly reverses within 1 to 4 h, and a significant increase in both the total WBC count and PMNs usually occurs.

The difficulty in early diagnosis of sepsis is reflected by the high morbidity and mortality associated with the disease. Overall mortality in patients with septic shock ranges from 25 to 90%, and poor results often follow failure to institute therapy soon enough. However, experimental trials of therapy with monoclonal antibodies to the lipid A fraction of the endotoxin, antileukotrienes, and antibodies to tumor necrosis factor have been unsuccessful. Glucocorticoids are now of no routine benefit, although they may have a place in selected types of infection, such as meningitis, and in patients with adrenal insufficiency.

A need, therefore, exists for a method of diagnosing sepsis sufficiently early to allow effective intervention and prevention. There is a further need for the development of effective treatment for sepsis. The present invention addresses these needs.

SUMMARY OF THE INVENTION

Methods are provided for the prediction and diagnosis of sepsis through measurement of neurotensin levels taken from a biological sample of a patient, particularly a blood sample, e.g. plasma, serum, etc. Samples may be obtained from an individual at risk of developing sepsis and other systemic inflammatory response syndromes, having sepsis and other systemic inflammatory response syndromes, suspected of having sepsis and other systemic inflammatory response syndromes, etc. The level of neurotensin in a test, or patient sample is compared to a reference value, for example a value obtained from reference population known to have sepsis, and/or a reference population known to be negative for sepsis.

It is further shown herein that mast cells reduce concentrations of neurotensin in vivo, and that such reduction improves survival of the patient. In some embodiments of the invention methods are provided for the identification of agents, e.g. small organic compounds, antibodies, etc. that enhance survival from sepsis and other systemic inflammatory response syndromes by inhibiting neurotensin activity, which inhibition may be accomplished through downregulation of neurotensin activity, enhancement of neurotensin degradation, e.g. degradation by mast cells; enzymatic degradation including degradation by neurolysin; upregulation or administration of neurolysin; small molecule inhibition of neurotensin; reducing the ability of neurotensin to bind to neurotensin receptors; and the like.

In other embodiments, methods are provided for treatment of sepsis and other systemic inflammatory response syndromes, where the methods comprising administering to a patient suffering from sepsis and other systemic inflammatory response syndromes or at risk of sepsis and other systemic inflammatory response syndromes an agent that downregulates neurotensin activity, e.g. compounds that bind to and inhibit neurotensin, such as antibodies, small molecules, etc., agents that enhance neurotensin degradation, e.g. degradation by mast cells; enzymatic degradation including degradation by neurolysin; upregulation or administration of neurolysin; small molecule inhibition of neurotensin; reducing the ability of neurotensin to bind to neurotensin receptors; and the like.

DETAILED DESCRIPTION OF THE EMBODIMENTS

Figure 1:
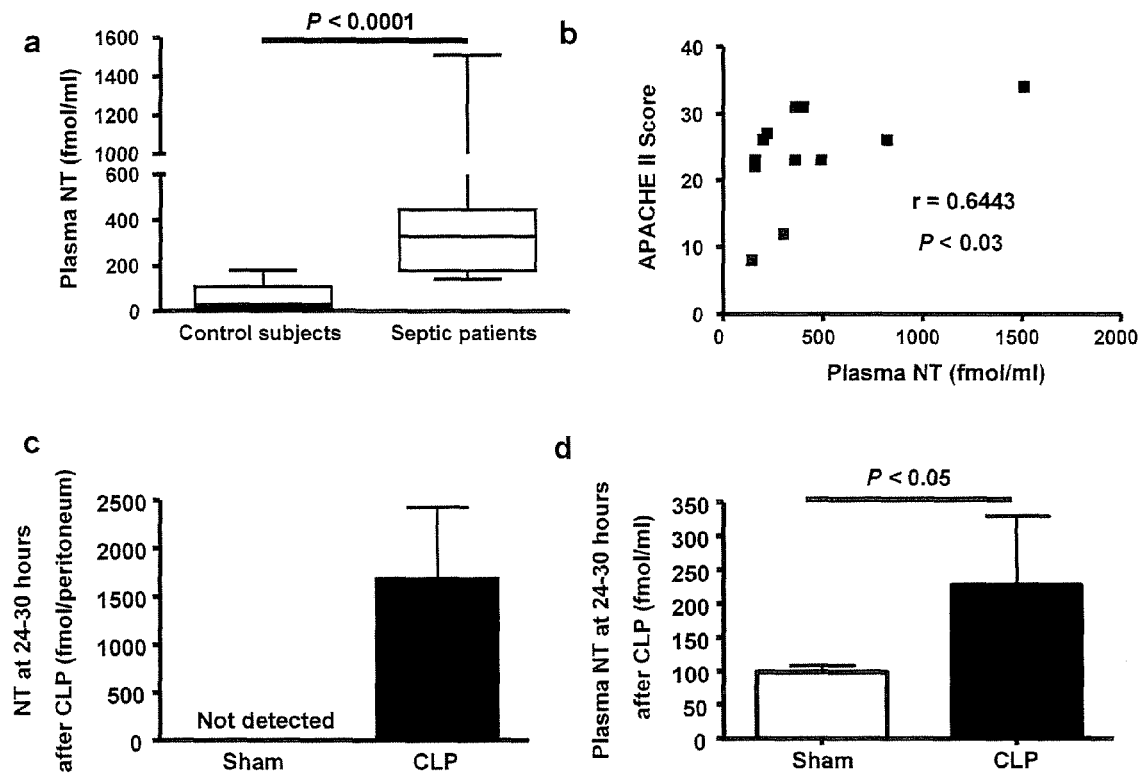
FIGS. 1a-d. Plasma neurotensin (NT) levels in septic humans and in a mouse model of sepsis. (a) Plasma concentrations of NT in healthy individuals (Control subjects) (n=14) and patients with sepsis (n=12). The bottom, median and top lines of the box mark the $25^{th}$, $50^{th}$ and $75^{th}$ percentiles, respectively. (b) Correlation between APACHE II score and plasma concentrations of NT in the 12 septic patients. (c, d) Concentrations of NT in the plasma (c) and peritoneal lavage fluid (d) at 24-30 h after induction of severe cecal ligation and puncture (CLP) (⅔ ceacal ligation; one puncture with a 20 G needle) in 12-week old female Kit$^{+/+}$ (wild type) mice.

The present invention allows for the diagnosis or prediction of sepsis and other systemic inflammatory response syndromes by analysis of the presence of neurotensin in a biological sample of a patient, particularly a blood sample, e.g. plasma, serum, etc. Advantageously, sepsis may be diagnosed or predicted prior to the onset of clinical symptoms, thereby allowing for more effective therapeutic intervention. In some embodiments of the invention methods are provided for the identification of agents, e.g. small organic compounds, antibodies, etc. that enhance survival from sepsis and other systemic inflammatory response syndromes by inhibiting neurotensin activity or by antagonizing the action of neurotensin at neurotensin receptors. Methods are also provided for alleviating the pathology of sepsis by administration of neurotensin inhibiting agents or by antagonizing the action of neurotensin at neurotensin receptors.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

As summarized above, the subject invention is directed to methods of classification of patients according to the presence of neurotensin, and presence of sepsis, as well as reagents and kits for use in practicing the subject methods. The methods may also determine a treatment for sepsis.

Methods are also provided for optimizing therapy, by first classification, and based on that information, selecting the appropriate therapy, dose, treatment modality, etc. which optimizes the differential between delivery of a treatment, while minimizing undesirable toxicity.

Neurotensin. Neurotensin (NT) is a tridecapeptide that is found in a variety of peripheral and central tissues where it is involved in a number of effects, including modulation of central dopaminergic and cholinergic circuits, thermoregulation, intestinal motility, and blood pressure regulation. Neurotensin is also one of the most potent antinociceptive substances known, and an inhibitor of neurolysin has been shown to produce neurotensin-induced analgesia in mice. widely distributed throughout the central nervous system.

The human peptide has the sequence (SEQ ID NO:1): QLYENKPRRPYIL. The propeptide from which it is cleaved has the sequence (SEQ ID NO:2) MMAGMKIQLV CMLLLAFSSW SLCSDSEEEM KALEADFLTN MHTSKISKAH VPSWKMTLLN VCSLVNNLNS PAEET-GEVHE EELVARRKLP TALDGFSLEA MLTIYQLHKI CHSRAFQHWE LIQEDILDTG NDKNGKEEVI KRKIPY-ILKR QLYENKPRRP YILKRDSYYY. The precursor protein also gives rise to the closely related peptide neuromedin (NN). The four amino acids at the carboxy terminal of NT and NN are identical, and amino acids 8-13 of NT are essential for biologic activity. The NT/neuromedin N(NT/NN) gene is highly conserved between species.

Elements involved in the regulation of NT/NN mRNA expression are located in the upstream 200-bp flanking region of the gene. In this region, several cis-regulatory elements function cooperatively to integrate multiple environmental stimuli into a concerted transcriptional response. These sites include a consensus AP-1 site, two near consensus cyclic AMP response elements, one near consensus glucocorticoid response element, and a sequence identical to the human c-jun gene autoregulatory element. The glucocorticoid response element is absent in the regulatory sequence of the human NT/NN gene.

In neurons, NT is stored in dense core vesicles and released in a $Ca^{2+}$-dependent manner. NT transmission is terminated primarily by cleavage of NT by several peptidases, including neutral endopeptidase 24.11, angiotensin-converting enzyme, metalloendopeptidase 24.15, and metalloendopeptidase 24.16. In brain tissue, the reported half-life of NT is approximately 15 min.

Receptors for NT include a receptor with low affinity for NT (NTRL, Ntsr2 or NTR2); a receptor with high affinity for NT (NTRH, Ntsr1 or NT1), and a third NT receptor (NTR3, Ntsr3 or NT3) that is located intracellularly and has been identified as the previously characterized gp95/sortilin. Both NTR1 and NTR2 are G-protein coupled receptors with the typical 7-transmembrane configuration characteristic of these receptors. NTR1 or NTR2 activation not only leads to an activation of second messenger pathways, but also changes the affinity of dopamine receptors via allosteric receptor/receptor interactions and modulates gene expression via the internalized NT-NTR1/2 complex. NTR3 is a type I amino acid receptor with a single transmembrane-spanning region. NTR3 is located in glia, neurons, and adipocytes and is believed to be involved in the sorting of luminal proteins from the trans-Golgi to late endosomes. NTR3 may also be involved in modulation of NT signal termination via mediation of NT uptake and degradation.

NTR agonists include modified subfragments of the NT peptide itself and the neurotensin analogue PD149163 (see Azmi et al. (2006) Behav Pharmacol. 17(4):357-62. Several nonpeptide NTR antagonists have been identified of which SR48692 and SR142948A are the best characterized (for example, see Gully et al. (1993) Proc Natl Acad Sci USA. 1993 90(1): 65-69; and Gully et al. J Pharmacol Exp Ther (1997) 280: 802-812). Both of these antagonists possess nanomolar affinity for NTR1 in different tissues and cells from various species. SR142948A, however, has a higher affinity for NTR1 than SR48692, and only SR142948A binds NTR2 with nanomolar affinity.

Neurolysin. Neurolysin (EC 3.4.24.16) is an endopeptidase that cleaves a number of neuropeptides. In vivo it has been shown to be involved in metabolism of neurotensin, hydrolyzing the peptide between residues 10 and 11, creating inactive fragments. In addition the enzyme EC 3.4.24.15 hydrolyses NT exclusively at the $Arg^8$-$Arg^9$ bond. The amino acid sequence of neurolysins are known in the art, for example the human protein sequence may be found in Genbank, accession no. NP_065777, (see also Serizawa et al., (1995) J. Biol. Chem. 270(5):2092-2098).

The enzyme is a neutral metalloendopeptidase with a zinc containing catalytic core, inhibited by metal ion chelators, and can be reactivated by divalent cations. The zinc atom is coordinated by the side chains of the two active-site histidines, plus a glutamate residue located 25 residues carboxy terminal to the second His. The active-site Glu also participates in the coordination of the zinc, via an activated water molecule.

"Systemic inflammatory response syndrome", or "SIRS", refers to a clinical response to a variety of severe clinical insults, for example as manifested by two or more of the following conditions within a 24-hour period: body temperature greater than 38° C. or less than 36° C.; heart rate (HR) greater than 90 beats/minute; respiratory rate (RR) greater than 20 breaths/minute, or $P_{CO2}$ less than 32 mm Hg, or requiring mechanical ventilation; and white blood cell count (WBC) either greater than $12 \times 10^9$/L or less than $4 \times 10^9$/L or having greater than 10% immature forms (bands). SIRS may result from a variety of conditions, including trauma such as burns or other insults, including sepsis.

Sepsis refers to a serious infection, localized, bacteremic or fungal, that is accompanied by systemic manifestations of inflammation. The term "onset of sepsis" refers to an early stage of sepsis, i.e. prior to a stage when the clinical manifestations are sufficient to support a clinical suspicion of sepsis. "Severe sepsis" refers to sepsis associated with organ dysfunction, hypoperfusion abnormalities, or sepsis-induced hypotension. Hypoperfusion abnormalities include, but are not limited to, lactic acidosis, oliguria, or an acute alteration in mental status. "Septic shock" refers to sepsis-induced hypotension that is not responsive to adequate intravenous fluid challenge and with manifestations of peripheral hypoperfusion.

As used herein, an "individual" is an animal, usually a mammal, more usually a human or non-human primate. The terms "individual", "subject" and "patient" are used interchangeably herein. The individual can be normal, suspected of having SIRS or sepsis, at risk of developing SIRS or sepsis, or confirmed as having SIRS or sepsis.

Individuals having a variety of physiological conditions corresponding to the various stages in the progression of sepsis or SIRS, from the absence of sepsis or SIRS to severe sepsis or SIRS, may be distinguished by the presence of elevated levels on neurotensin in the blood or plasma. Such individuals may be treated by methods that reduce neurotensin activity.

Polypeptides

Neurotensin polypeptides are of interest for screening methods, as reagents to raise antibodies, and the like. Neurolysin polypeptides are also of interest, e.g. as therapeutic agents. Such polypeptides can be produced through isolation from natural sources, recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity as the polypeptide encoded by native neurotensin.

The polypeptides may be produced by recombinant DNA technology using techniques well known in the art. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

The polypeptide may be labeled, either directly or indirectly. Any of a variety of suitable labeling systems may be used, including but not limited to, radioisotopes such as $^{125}$I; enzyme labeling systems that generate a detectable calorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by a Fab expression library.

Once synthesized, the polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)).

Antibodies

Antibodies that selectively bind to neurotensin are of interest for diagnostic and therapeutic purposes. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a neurotensin antigen comprising an antigenic portion of the polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Fruend's, Fruend's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the brain tumor protein target, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT). Large quantities of monoclonal antibodies from the secreting hybridomas may then be produced by injecting the clones into the peritoneal cavity of mice and harvesting the ascites fluid therefrom.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Antibodies with a reduced propensity to induce a violent or detrimental immune response in humans (such as anaphylactic shock), and which also exhibit a reduced propensity for priming an immune response which would prevent repeated dosage with the antibody therapeutic or imaging agent are preferred for use in the invention. Thus, humanized, single chain, chimeric, or human antibodies, which produce less of an immune response when administered to humans, are preferred for use in the present invention.

A chimeric antibody is a molecule in which different portions are derived from different animal species, for example those having a variable region derived from a murine mAb and a human immunoglobulin constant region. Techniques for the development of chimeric antibodies are described in the literature. See, for example, Morrison et al. (1984) *Proc. Natl. Acad. Sci.* 81:6851-6855; Neuberger et al. (1984) *Nature* 312:604-608; Takeda et al. (1985) *Nature* 314:452-454. Single chain antibodies are formed by linking the heavy and light chain fragments of the Fv region via an amino acid bridge, resulting in a single chain polypeptide. See, for example, Huston et al., *Science* 242:423-426; Proc. Natl. Acad. Sci. 85:5879-5883; and Ward et al. *Nature* 341:544-546.

Antibody fragments that recognize specific epitopes may be generated by techniques well known in the field. These fragments include, without limitation, Fv, F(ab')$_2$ fragments, which can be produced by pepsin digestion of the antibody molecule, and Fab fragments, which can be generated by reducing the disulfide bridges of the F(ab')$_2$ fragments.

Humanized antibodies are human forms of non-human antibodies. They are chimeras with a minimum sequence derived from of non-human Immunoglobulin. To overcome the intrinsic undesirable properties of murine monoclonal antibodies, recombinant murine antibodies engineered to incorporate regions of human antibodies, also called "humanized antibodies" are being developed. This alternative strategy was adopted as it is difficult to generate human antibodies directed to human antigens such as cell surface molecules. A humanized antibody contains complementarity determining region (CDR) regions and a few other amino acid of a murine antibody while the rest of the antibody is of human origin.

In addition, derivatized immunoglobulins with added chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention. For convenience, the term "antibody" or "antibody moiety" will be used throughout to generally refer to molecules which specifically bind to neurotensin, although the term will encompass all immunoglobulins, derivatives, fragments, recombinant or engineered immunoglobulins, and modified immunoglobulins, as described above.

Candidate anti-neurotensin antibodies can be tested for by any suitable standard means, e.g. ELISA assays, etc. As a first screen, the antibodies may be tested for binding against the immunogen. After selective binding is established, the candidate antibody, or an antibody conjugate, may be tested for appropriate activity in an in vivo model, for example as provided in the Examples. These methods include, but are not limited to, methods that measure binding affinity to a target, biodistribution of the compound within an animal or cell, or compound mediated cytotoxicity. These and other screening methods known in the art provide information on the ability of a compound to bind to, modulate, or otherwise interact with the specified target and are a measure of the compound's efficacy.

Diagnostic and Prognostic Methods

The differential presence of neurotensin in blood samples of sepsis patients indicates that it can serve as a marker for diagnosis, as well as for therapeutic applications. In general, such diagnostic methods involve detecting an elevated level of neurotensin in bodily fluids or cells of an individual or a sample therefrom. A variety of different assays can be utilized to detect an increase in expression. More specifically, the diagnostic and prognostic methods disclosed herein involve obtaining a sample from an individual and determining at least qualitatively, and preferably quantitatively, the level of neurotensin in the sample, and correlating such level with a diagnosis of sepsis. Usually this determined value or test value is compared against a reference or baseline value, which may be a negative control value from a normal patient, and/or a positive control value from a known sepsis sample.

Samples can be obtained from a variety of sources. Samples are typically obtained from a human subject. However, the methods can also be utilized with samples obtained from various other mammals, such as primates, e.g. apes and chimpanzees, horses and other farm animals, zoo animals, mice, cats, rats, and other animals. Such samples are referred to as a patient sample.

Samples can be obtained from the tissues or fluids of an individual, as well as from cell cultures or tissue homogenates. For example, samples can be obtained from blood, plasma, ascites, synovial fluid, CFS, etc. Also included in the term are derivatives and fractions of such cells and fluids. Samples can also be derived from in vitro cell cultures, including the growth medium, recombinant cells and cell components. Diagnostic samples are collected from an individual that has, or is suspected to have, sepsis and other systemic inflammatory response syndromes, or is in danger of developing sepsis and other systemic inflammatory response syndromes, e.g. a burn or trauma victim, etc.

Screening for expression of the subject sequences may be based on the functional or antigenic characteristics of the protein. A method for diagnosis may utilize in vitro detection of binding between antibodies and neurotensin in a sample, e.g. blood, plasma, etc. Measuring the concentration of the target protein in a sample or fraction thereof may be accomplished by a variety of specific assays. A conventional sandwich type assay may be used, e.g. ELISA. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of the test protein is assayed in parallel with the samples or aliquots thereof to serve as controls. Preferably, each sample and standard will be added to multiple wells so that mean values can be obtained for each. The incubation time should be sufficient for binding. After incubation, the insoluble support is generally washed of nonbound components. After washing, a solution containing a second antibody is applied. The antibody will bind to one of the proteins of interest with sufficient specificity such that it can be distinguished from other components present. The second antibodies may be labeled to facilitate direct, or indirect quantification of binding. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules.

After the second binding step, the insoluble support is again washed free of non-specifically bound material, leaving the specific complex formed between the target protein and the specific binding member. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the targeted polypeptide, conveniently using a labeling method as described for the sandwich assay.

Arrays provide a high throughput technique that can assay a large number of polypeptides in a sample. In one aspect of the invention, an array is constructed comprising one or more antibodies that specifically bind to neurotensin, and may further comprise antibodies for the additional markers as previously described. This technology is used as a tool to quantitate expression. Arrays can be created by spotting a probe onto a substrate (e.g., glass, nitrocellulose, etc.) in a two-dimensional matrix or array having bound probes. The probes can be bound to the substrate by either covalent bonds or by non-specific interactions, such as hydrophobic interactions. Techniques for constructing arrays and methods of using these arrays are described in, for example, Schena et al., (1996) *Proc Natl Acad Sci USA*. 93(20):10614-9; Schena et al., (1995) *Science* 270(5235):467-70; Shalon et al. (1996) *Genome Res.* 6(7):639-45, U.S. Pat. No. 5,807,522, EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734. The probes utilized in the arrays can be of varying types and can include, for example, antibodies, including antibody fragments or peptidomimetics, peptides, proteins, and the like. Arrays can be utilized in detecting differential expression levels.

Common physical substrates for making protein arrays include glass or silicon slides, magnetic particles or other micro beads, functionalized with aldehyde or other chemical groups to help immobilize proteins. The substrate can also be coated with PLL, nitrocellulose, PVDF membranes or modified with specific chemical reagents to adsorb capture agents. The desirable properties of an ideal surface include: chemical stability before, during, and after the coupling procedure, suitability for a wide range of capture agents (e.g., hydrophilic and hydrophobic, low MW and high MW), minimal non-specific binding, low or no intrinsic background in detection, presentation of the capture agents in a fully-functional orientation, production of spots with predictable and regular morphology (shape, signal uniformity).

Both direct labeling and sandwich format approaches may find use. In the direct labeling procedure, the antibody array is interrogated with serum samples that had been derivatized with a fluorescent label, e.g. Cy3, Cy5 dye, etc. In the sandwich assay procedure, unlabeled serum is first incubated with the array to allow target proteins to be captured by immobilized capture antibodies. Next, the captured target proteins are detected by the application of a labeled detection antibody. The sandwich assay provides extra specificity and sensitivity needed to detect pg/mL concentrations of cytokines, without compromising the binding affinities of the target protein through a direct labeling procedure.

Fluorescence intensity can be determined by, for example, a scanning confocal microscope in photon counting mode. Appropriate scanning devices are described by e.g., U.S. Pat. No. 5,578,832 to Trulson et al., and U.S. Pat. No. 5,631,734 to Stern et al., and are available from Affymetrix, Inc., under the GeneChip™ label. Some types of label provide a signal that can be amplified by enzymatic methods (see Broude, et al., *Proc. Natl. Acad. Sci. U.S.A.* 91, 3072-3076 (1994)). A variety of other labels are also suitable including, for example, radioisotopes, chromophores, magnetic particles and electron dense particles.

Other methodologies also find use. In some embodiments, a solution based methodology utilizes capillary electrophoresis (CE) and microfluidic CE platforms for detecting and quantitating protein-protein interactions, including antibody reactions with serum proteins associated with atherosclerosis. This technique can be performed easily by any laboratory with access to a standard CE DNA sequencing apparatus. With this methodology, a fluorescent marker (eTag reporter) is targeted to the analyte with one antibody, and a second sandwich antibody of different epitope specificity that is chemically coupled to a "molecular scissors" induces release of the fluorescent probe when both antibodies are in close apposition on the specific analyte. Quantitation then is focused on the liberated eTag, that is quantified with a standard DNA capillary sequencing device. The eTag Assay System can be used to measure the abundance of multiple proteins simultaneously. A critical feature of the assay is that the affinity agents (antibodies) are not immobilized on surfaces, as is required with array technologies. Solution-based binding eliminates surface-induced denaturation and non-specific binding, and improves sensitivity and reaction kinetics. By combining different colors in the eTag reporters, both mobility and color may be used to dramatically increase the degree of multiplexing. Many binding reactions can be multiplexed in the same vessel, followed by CE to identify the released eTag reporters. Each released eTag reporter encodes the identity of the probe to which it was originally attached. As a result, it is straightforward to configure multiplexed assays to monitor various types of molecular recognition events, especially protein-protein binding.

In some cases, a competitive assay will be used. In addition to the patient sample, a competitor to the targeted protein is added to the reaction mix. The competitor and the target compete for binding to the specific binding partner. Usually, the competitor molecule will be labeled and detected as previously described, where the amount of competitor binding will be proportional to the amount of target protein present. The concentration of competitor molecule will be from about 10 times the maximum anticipated protein concentration to about equal concentration in order to make the most sensitive and linear range of detection.

Therapeutic/Prophylactic Treatment Methods

Agents that modulate activity of neurotensin provide a point of therapeutic or prophylactic intervention, particularly agents that block binding of NT to its receptors, inhibit activity of the polypeptide, increase degradation of the polypeptide, or inhibit expression of the gene. In one embodiment of the invention, an antibody as described above is administered for treatment or prevention of sepsis. This antibody may be a neutralizing antibody, a functional blocker, may bind to and prevent receptor binding, etc. In an alternative embodiment, neurolysin is administered for treatment or prevention of sepsis, in a dose effective to neutralize the neurotensin present in the patient plasma at the time of sepsis.

Agents useful in modulating neurotensin activity include agents that directly modulate expression, e.g. expression vectors, antisense specific for the targeted polypeptide; and agents that act on the protein, e.g. specific antibodies and analogs thereof, small organic molecules that block catalytic activity or receptor binding, etc.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will be different from patient to patient. A competent clinician will be able to determine an effective amount of a therapeutic agent to administer to a patient to retard the growth and promote the death of tumor cells, or an effective amount of an imaging composition to administer to a patient to facilitate the visualization of a tumor. Dosage of an antibody, neurolysin, etc. will depend on the treatment of the patient, route of administration, the nature of the therapeutics, etc. Utilizing $LD_{50}$ animal data, and other information available, a clinician can determine the maximum safe dose for an individual, depending on the route of administration. Compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

The compositions can be administered to the subject in a series of more than one administration, although in some cases a single dose during the acute stage will be sufficient. For therapeutic compositions, regular periodic administration (e.g., daily) may sometimes be required, or may be desirable to reduce toxicity. For therapeutic compositions which will be utilized in repeated-dose regimens, compounds that do not provoke immune responses are preferred.

Compound Screening

Compound screening may be performed using an in vitro model, a genetically altered cell or animal, or purified neurotensin protein. One can identify ligands or substrates that bind to, modulate or mimic the action of neurotensin, of an effect on mast cell degradation of neurotensin, and the like. Candidate agents in cell-free assays are desirably screened for activity in biological assays, e.g. in cell culture systems involving the interaction between mast cells and neurotensin, in animal models for sepsis, and the like.

Transgenic animals or cells derived therefrom are also used in compound screening. Transgenic animals may be made through homologous recombination, where the normal locus corresponding to neurotensin, neurolysin, etc. is altered. Alternatively, a nucleic acid construct is randomly integrated into the genome. Vectors for stable integration include plasmids, retroviruses and other animal viruses, YACs, and the like. A series of small deletions and/or substitutions may be made in the coding sequence to determine the role of different exons in enzymatic activity, oncogenesis, signal transduction, etc. Specific constructs of interest include antisense sequences that block expression of the targeted gene and expression of dominant negative mutations. A detectable marker, such as lac Z may be introduced into the locus of interest, where up-regulation of expression will result in an easily detected change in phenotype. One may also provide for expression of the target gene or variants thereof in cells or tissues where it is not normally expressed or at abnormal times of development. By providing expression of the target protein in cells in which it is not normally produced, one can induce changes in cell behavior.

Compound screening identifies agents that modulate function of neurotensin. Of particular interest are screening assays for agents that have a low toxicity for human cells. A wide variety of assays may be used for this purpose, including labeled in vitro protein-protein binding assays, and the like. Knowledge of the 3-dimensional structure of the encoded protein, derived from crystallization of purified recombinant protein, could lead to the rational design of small drugs that specifically inhibit activity.

The term "agent" as used herein describes any molecule, e.g. protein or pharmaceutical, with the capability of altering or mimicking the physiological function of neurotensin. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to neurotensin polypeptide, as at least some of the compounds so identified are likely to be neurotensin antagonists. The binding assays usually involve contacting neurotensin with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89.

Compounds that are initially identified by any of the foregoing screening methods can be further tested to validate the apparent activity. The basic format of such methods involves administering a lead compound identified during an initial screen to an animal that serves as a model for humans and then determining the effect of sepsis, or the effect on mast cell degradation of neurotensin. The animal models utilized in validation studies generally are mammals. Specific examples of suitable animals include, but are not limited to, primates, mice, and rats.

Active test agents identified by the screening methods described herein that inhibit neurotensin activity can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Kits

The invention also provides kits that are useful in determining the status of sepsis or diagnosing SIRS in an individual. The kits of the present invention comprise reagents for detection of neurotensin, e.g. antibodies specific for neurotensin. The kit may also comprise at least one internal standard to be used in generating a neurotensin profile for diagnosis of sepsis. The antibodies themselves may be detectably labeled. The kit also may comprise a specific neurotensin binding component, such as an aptamer.

Kits of the present invention may also include pharmaceutical excipients, diluents and/or adjuvants. Examples of pharmaceutical adjuvants include, but are not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It may also be desirable to include isotonic agents such as sugars, sodium chloride, and the like.

EXAMPLES

The following examples are representative of the embodiments encompassed by the present invention and in no way limit the subject embraced by the present invention.

Example 1

Sepsis is a complex, incompletely understood and often fatal disorder, typically accompanied by hypotension, that is considered to represent a dysregulated host response to an infection. Neurotensin (NT) is 13-amino-acid peptide that, among its multiple effects, induces hypotension. It was found that plasma concentrations of NT are increased in humans with sepsis and in mice after caecal ligation and puncture (CLP), a model of sepsis. In mice, mast cells can degrade NT through neurotensin receptor 1- and neurolysin-dependent mechanisms, diminish the hypotensive effects of NT, and reduce intraperitoneal NT concentrations and improve survival after CLP. These findings show that mast cells can regulate NT concentrations in mice, and identify NT as a biomarker and therapeutic target in sepsis.

Plasma concentrations of NT were markedly elevated in patients with sepsis (median: 330 fmol/ml [range: 142-1508 fmol/ml, n=12], versus a median of 30 fmol/ml [range: 13.8-180 fmol/ml, n=14] in healthy subjects, P<0.0001) (FIG. 1a). Moreover, there was a significant positive correlation between plasma concentrations of NT in septic patients and their APACHE II score, a measure of the clinical severity of this disorder (FIG. 1b, Table 1). In addition to NT, we measured endothelin-1 (ET-1) and tumor necrosis factor (TNF), two mediators whose levels can be increased in the blood of some patients with sepsis. ET-1 was detected in the plasma of some of the septic patients (median: 19 fmol/ml [range: 0.8-38 fmol/ml, n=6]), but in none of the control samples; TNF was not detectable in any of the samples. As expected, septic patients had elevated plasma concentrations of C-reactive protein (CRP) (Table 1), a non-specific marker of inflammation.

TABLE 1

Characteristics of normal control subjects and patients with sepsis (as assessed within 24 h of admission to the intensive care unit)

|  | Control subjects (n = 14) | Septic Patients (n = 12) |
| --- | --- | --- |
| Age* | 50.7 ± 1.7 | 52.1 ± 4.6 |
| Gender (% M/% F) | 64/36 | 83/17 |
| Etiological agent of sepsis: G+ bacteria/G– bacteria/unknown (n) | n/a | 4/4/4 |
| APACHE II score* | n/a | 23.8 ± 2.2 |
| C-reactive protein (normal range: 0-5 mg/L)* | 1.78 ± 0.71 | 224.7 ± 33.8 | n/a: not applicable.
*Data are presented as mean ± SEM.

Figure 2:
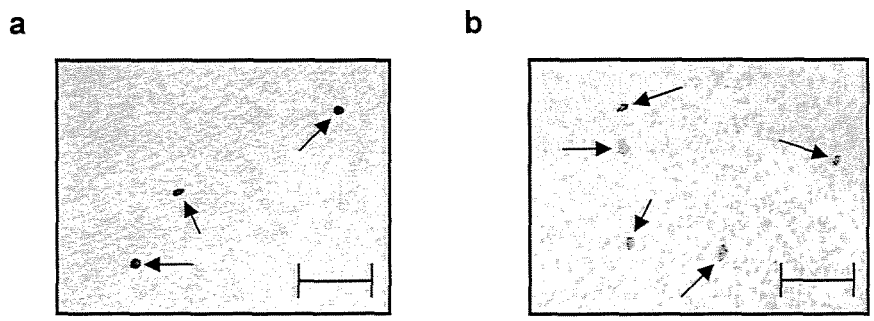
FIG. 2. Mast cells (MCs) in the mesentery (arrows, MCs; scale bars, 100 µm; Czaba stain) of (a) NT+/+ (wild type) mice and (b) NT−/− mice.
Figure 3:
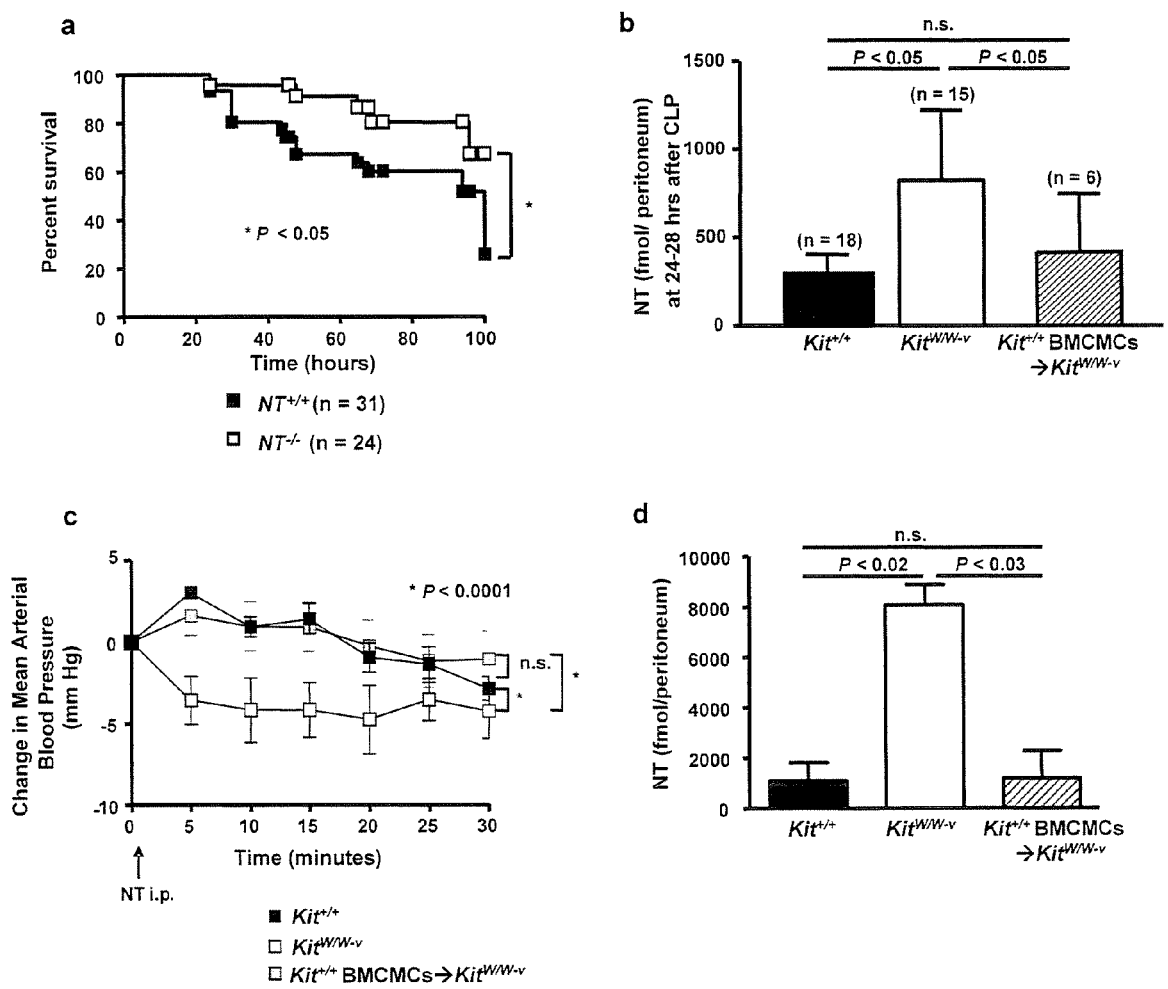
FIGS. 3a-d. NT promotes hypotension and contributes to mortality in CLP, and mast cells (MCs) reduce NT concentrations in CLP or after injection of NT. (a) Survival after CLP (50% ligation; single puncture with 20 G needle) in wild type (NT$^{+/+}$) and in NT-deficient (NT$^{−/−}$) mice. (b) NT levels in the peritoneal lavage fluid at 24-28 h after CLP (50% ligation; single puncture with 22 G needle) in wild type (Kit$^{+/+}$), Kit$^{W/W-v}$ MC-deficient or Kit$^{+/+}$ MC-engrafted Kit$^{W/W-v}$ (Kit$^{+/+}$ mouse bone marrow-derived MCs [BMCMCs]→Kit$^{W/W-v}$) mice. Data were pooled from three experiments that gave similar results. (c) Changes in mean arterial pressure (MAP) versus baseline levels (="0", measured 3 min after injection of 300 µl saline, i.p.) at various times after injection of NT (6 nmol in 300 µl saline, i.p.), and (d) NT levels in the peritoneal fluids of these mice at 30 min after injection of NT, in wild type (Kit$^{+/+}$), Kit$^{W/W-v}$ MC-deficient or Kit$^{+/+}$ BMCMCs→Kit$^{W/W-v}$ mice.

NT concentrations also were elevated in the plasma (FIG. 1c) and peritoneal cavity (FIG. 1d) of mice after induction of CLP, a widely used model of sepsis. We therefore performed studies in $NT^{-/-}$ mice to evaluate whether NT might contribute to the pathology associated with CLP. $NT^{-/-}$ mice resemble wild type mice in general appearance, gross anatomy, body weight, reproduction and overt behavior. We found that $NT^{+/+}$ and $NT^{-/-}$ mice also had similar numbers of mast cells (MCs) in the peritoneal cavity (2.1±0.1% or 1.7±0.2%), and mesentery windows (FIG. 2). However, $NT^{-/-}$ mice exhibited significantly enhanced survival after CLP compared to that of the littermate control ($NT^{+/+}$) mice (FIG. 3a).

MCs can promote the survival of mice subjected to CLP, and MC activation by ET-1 can contribute to both MC-dependent regulation of ET-1 concentrations in the peritoneal cavity, and enhanced mouse survival, in this setting. In vitro studies show that certain MC populations also can be activated by NT. We found that intraperitoneal concentrations of NT were significantly higher in genetically MC-deficient $Kit^{W/W-v}$ mice than in the congenic normal ($Kit^{+/+}$) mice 24-28 h after CLP (FIG. 3b). To assess the extent to which this difference reflected the MC deficiency of $Kit^{W/W-v}$ mice, as opposed to other consequences of their c-kit mutations, we also analyzed $Kit^{W/W-v}$ mice that had been selectively engrafted i.p. with $Kit^{+/+}$ bone marrow-derived cultured MCs (BMCMCs) ($Kit^{+/+}$ BMCMCs→$Kit^{W/W-v}$ mice). Concentrations of NT in the peritoneal cavity after CLP in $Kit^{+/+}$ BMCMCs→$Kit^{W/W-v}$ mice were very similar to those in $Kit^{+/+}$ mice (FIG. 3b).

Taken together, our results indicate that NT can contribute to the mortality associated with CLP and that MCs can regulate NT concentrations in the peritoneal cavity after CLP.

Figure 4:
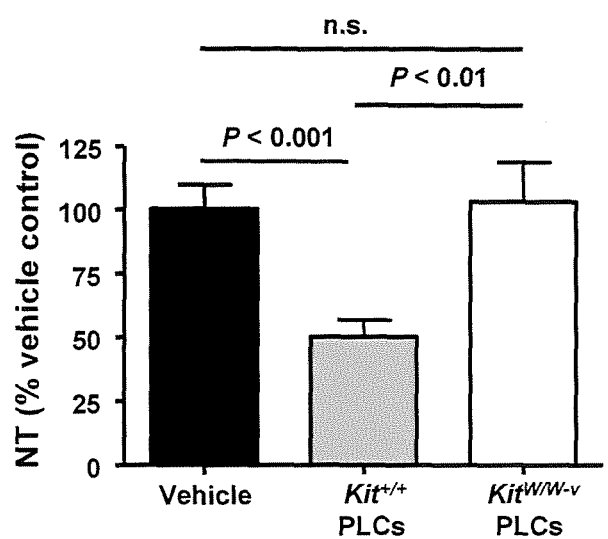
FIG. 4. Evidence that mast cells are the only peritoneal cells with the ability to degrade NT. NT (10 µM) was incubated for 30 min at 37° C. with PLCs containing 5×10$^4$ PMCs or with vehicle alone. Peritoneal lavage cells (PLCs) were obtained from Kit$^{+/+}$ or Kit$^{W/W-v}$ mast cell deficient mice. Results are expressed as the percentage of NT remaining in the samples incubated with cells compared to that in samples of NT incubated in vehicle alone at 37° C. (n=3).

Rat peritoneal MCs (PMCs) can degrade NT in vitro. In accord with that result, we found that peritoneal lavage cells (PLCs) of $Kit^{+/+}$ mice but not MC-deficient $Kit^{W/W-v}$ mice reduced concentrations of NT in vitro (FIG. 4). To assess whether MCs might be able to reduce levels of NT in vivo in mice not subjected to CLP, we administered NT i.p (6 nmol in 300l saline), and then measured mean arterial blood pressure (MAP). NT induced more significant reductions in MAP in $Kit^{W/W-v}$ mice than in $Kit^{+/+}$ or $Kit^{+/+}$ BMCMCs→$Kit^{W/W-v}$ mice (FIG. 3c). Moreover, 30 min after injection of NT, concentrations of NT were significantly higher in the peritoneal cavities of $Kit^{W/W-v}$ mice than in $Kit^{+/+}$ or $Kit^{+/+}$ BMCMCs→$Kit^{W/W-v}$ mice (FIG. 3d).

Figure 5:
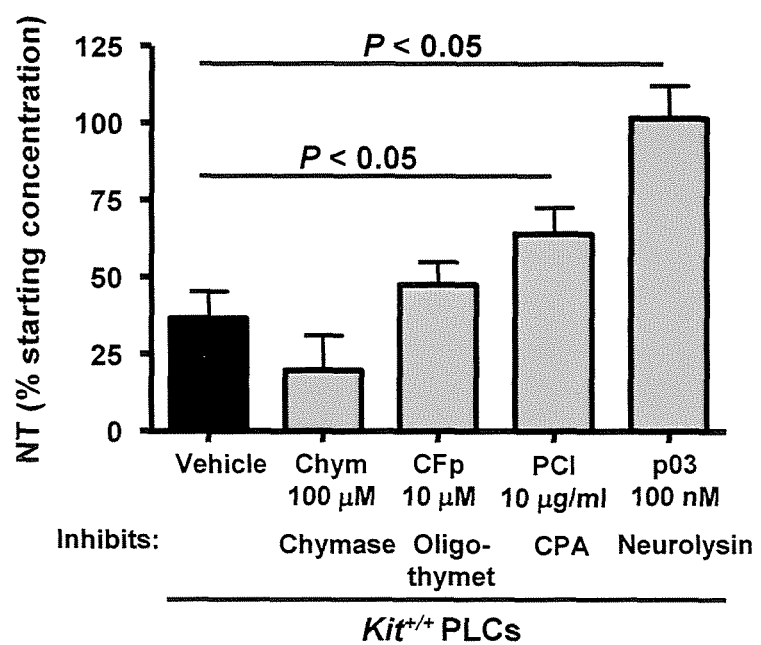
FIG. 5. Neurolysin and carboxypeptidase inhibitors prevent NT degradation by peritoneal mast cells. Kit$^{+/+}$ PLCs containing 5×10$^4$ PMCs were pre-treated for 15 min at 37° C. with one of the following protease inhibitors: chymostatin (chym, chymase inhibitor at 100 µM), CFp-Ala-Ala-Phe-pAB (CFp, oligo thymet inhibitor at 10 µM only for PLCs), potato carboxypeptidase inhibitor (PCI, carboxypeptidase inhibitor at 10 µg/ml) and phosphodiepryl 03 (p03, neurolysin inhibitor at 100 nM for PLCs. Cells were then incubated with NT (10 µM) for 30 min at 37° C. Results are the percentage of NT remaining after incubation with cells compared to the starting concentration of NT (n=4-9 per group).
Figure 6:
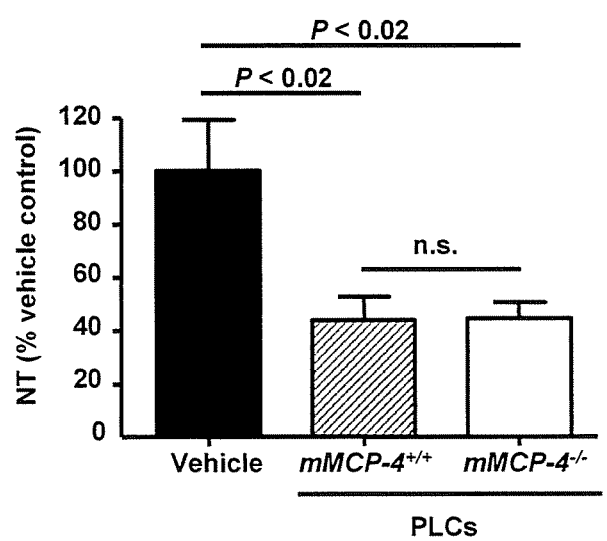
FIG. 6. Mouse mast cell protease-4 (mMCP-4) does not degrade NT. PLCs containing 5×10$^4$ peritoneal MCs (PMCs) obtained from either wild type mMCP-4 (mMCP-4$^{+/+}$) mice or mMCP-4-deficient (mMCP-4$^{−/−}$) mice were incubated with NT (10 µM) for 30 min at 37° C. Results are the percentage of NT remaining after incubation with cells compared to that in samples of NT incubated in vehicle alone at 37° C. (n=3).

We used pharmacological and genetic approaches to evaluate how MCs might be able to regulate concentrations of NT. Using inhibitors of various proteases that can degrade NT, we found that NT degradation by PLCs was significantly inhibited by the mouse MC carboxypeptidase A (mMC-CPA) inhibitor, PCI, and by the neurolysin (NLN) inhibitor, phosphodiepryl 03 (p03) (FIG. 5). The chymase inhibitor chymostatin (Chym) and the oligo thymet inhibitor CFp-Ala-Ala-Phe-pAB (CFp) did not prevent NT degradation by PLCs (FIG. 5). It has been reported that human skin chymase can degrade NT. However, we found that NT was degraded to the same extent by PLCs of wild type control mice and mouse MC protease-4 (mMCP-4)-deficient ($MCP-4^{-/-}$) mice, which lack mMCP-4, the major protease of mouse peritoneal MCs with chymotryptic activity (FIG. 6).

Figure 7:
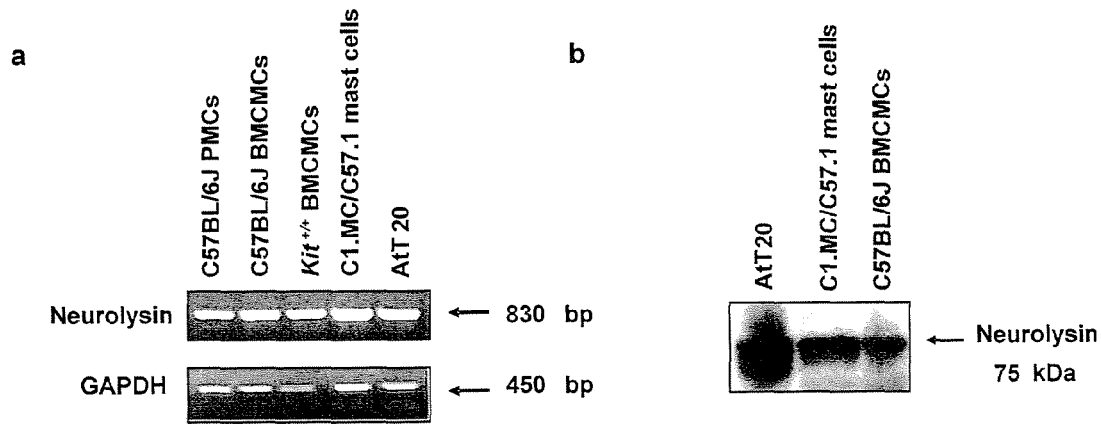
FIG. 7. Mast cells express neurolysin. (a), Expression of mRNA for neurolysin in the AtT20 neuroendocrine cell line (used as a positive control), the mast cell line C1.MC/C57.1, C57BL/6J BMCMCs, Kit$^{+/+}$ BMCMCs and peritoneal mast cells purified from Kit$^{+/+}$ mice (PMCs). (b), Western blot analysis for neurolysin in lysates of AtT20 cells, C1.MC/C57.1 mast cells and C57BL/6J BMCMCs.
Figure 8:
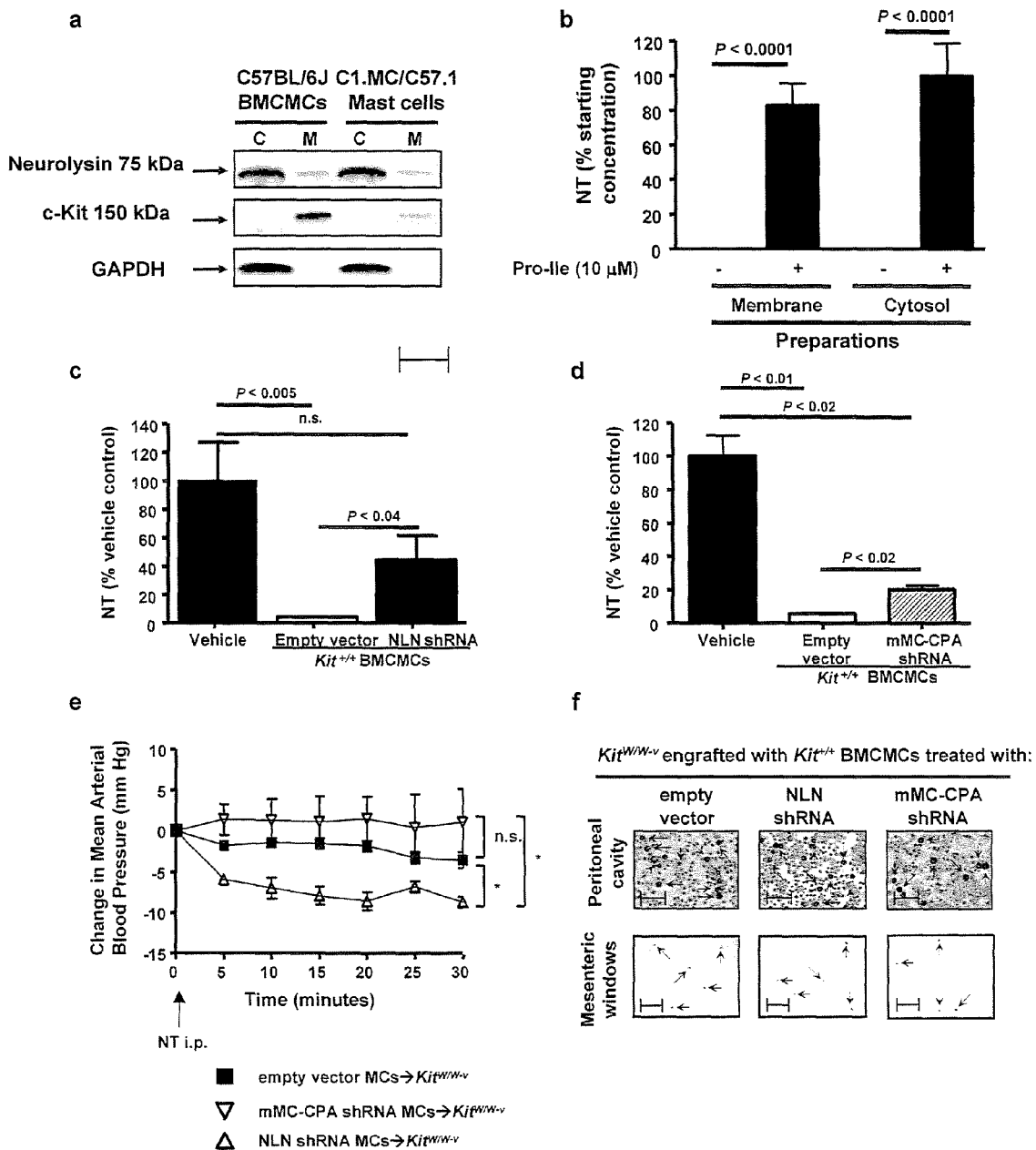
FIG. 8. MC-associated neurolysin (NLN) contributes to the MCs' ability to reduce NT-induced hypotension. (a) Identification of NLN in the membrane and cytosol fractions of C1.MC/C57.1 MCs and C57BL/6J BMCMCs. (b) Degradation of NT (10 µM) by membrane and cytosol preparations obtained from Kit$^{+/+}$ BMCMCs (2×10$^6$ cells/preparation) that were pre-treated with either vehicle or with Pro-Ile (10 µM, 15 min at 370° C.). Results are expressed as the percentage of NT remaining after incubation with membrane or cytosol preparations compared to that in samples of NT incubated in vehicle alone (n=3). (c, d) Degradation of NT (10 µM) by A23187 (5 µM)-activated Kit$^{+/+}$ BMCMCs (2×10$^5$) that were pre-treated with either empty vector, Neurolysin-short hairpin RNA (NLN-shRNA) or mouse MC carpoxypeptidase A-short hairpin RNA (mMC-CPA-shRNA). Cells were incubated with NT for 30 min at 37° C. Results are expressed as the percentage of NT remaining in the samples compared to that in samples of NT incubated in vehicle alone at 37° C. (n=3). (e) Changes in MAP versus baseline levels (="0", measured 3 min after injection of 300 µl saline, i.p.) at various times after injection of NT (6 nmol in 300 µl saline, i.p.) in Kit$^{W/W-v}$ mice which had been engrafted i.p. with Kit$^{+/+}$ BMCMCs treated with either empty vector (empty vector MCs→Kit$^{W/W-v}$), NLN-shRNA (NLN-shRNA MCs→Kit$^{W/W-v}$) or mMC-CPA-shRNA (mMC-CPA-shRNA MCs→Kit$^{W/W-v}$). (f) MCs in the peritoneal cavity (arrows, MCs; scale bars, 100 µm; May Grunwald-modified Giemsa stain) and mesentery (arrows, MCs; scale bars, 100 µm; Czaba stain).

We then assessed whether MCs might express NLN. We detected NLN mRNA and protein in mouse MCs (FIG. 7), and found that NLN was present in both the membrane and cytosol fractions of such cells (FIG. 8a). Moreover, either membrane or cytosol preparations of mouse BMCMCs degraded NT, an ability that was almost completely inhibited by the NLN inhibitor, Pro-Ile (10 mM) (FIG. 8b).

Figure 9:
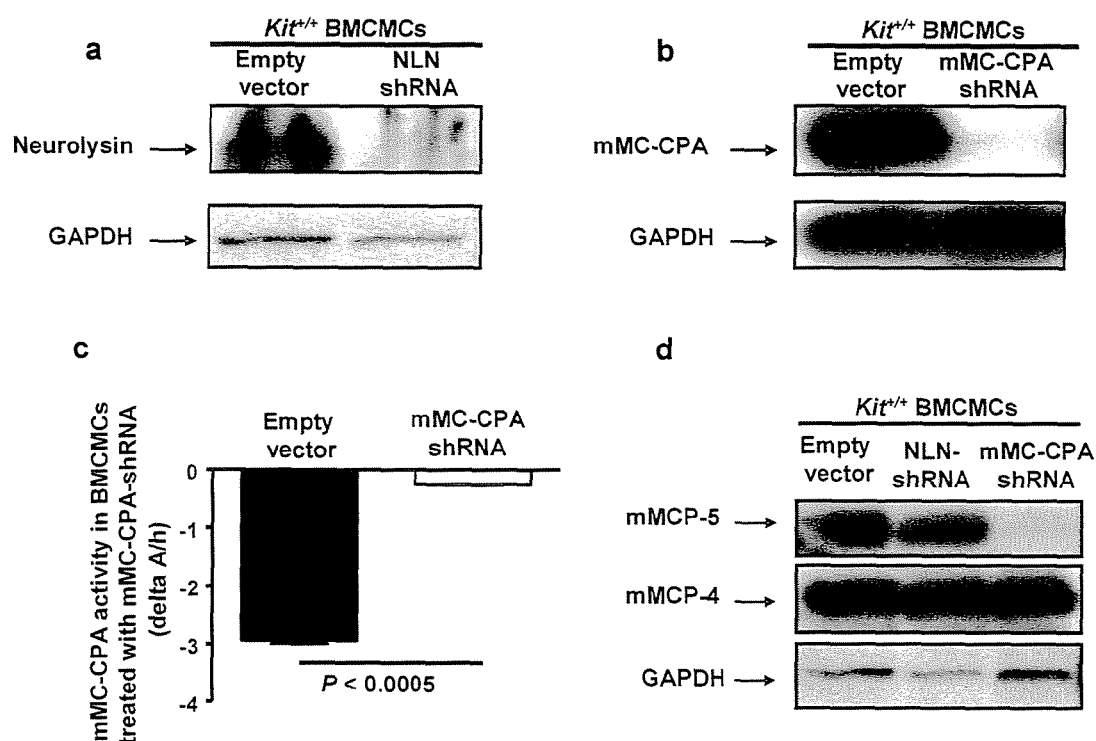
FIG. 9. Use of shRNA approach to knock-down NLN and mMC-CPA in BMCMCs. Protein expression for: (a), NLN and (b), mMC-CPA; and (c), mMC-CPA activity in Kit$^{+/+}$ BMCMCs treated with either empty vector or shRNAs. (d), mMCP-4 and mMCP-5 protein expression in Kit$^{+/+}$ BMCMCs treated with empty vector, NLN-shRNA or mMC-CPA-shRNA.
Figure 10:
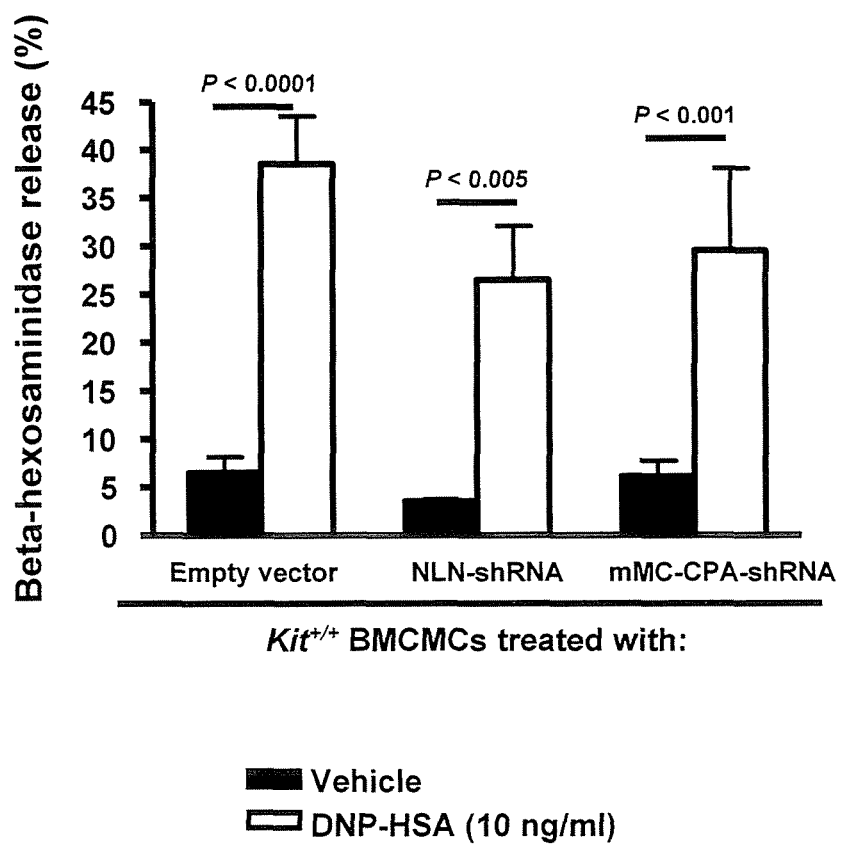
FIG. 10. BMCMCs treated with shRNAs degranulate after high affinity Fc receptor for IgE (FcεRI) cross-linking to the same extent than BMCMCs treated with empty vector. Beta-hexosaminidase release by Kit$^{+/+}$ BMCMCs treated with empty vector, NLN-shRNA for NLN or mMC-CPA-shRNA. Cells (1.25×10$^5$) were sensitized with IgE mAb to dinitrophenol (DNP, 2 µg/ml) overnight at 37° C. and then were challenged with DNP-human serum albumin (DNP-HSA, 10 ng/ml) for 30 min at 37° C.

It has been reported that PCI may inhibit NT degradation by rat MCs in part by interfering with the binding of NT to MCs, thus reducing MC degranulation. We therefore also used a non-pharmacological approach to assess the extent to which MC mMC-CPA or NLN can degrade NT in vitro. $Kit^{+/+}$ BMCMCs infected with a lentivirus that delivered short hairpin RNAs (shRNAs) to stably silence the expression of NLN or mMC-CPA exhibited reductions of 80% or 90% in protein expression levels for NLN or mMC-CPA, respectively (FIGS. 9a and 9b); mMC-CPA-shRNA-transduced BMCMCs also exhibited substantially reduced mMC-CPA enzymatic activity (FIG. 9c). In agreement with results reported for PMCs from mMC-CPA-deficient mice, the reduced levels of mMC-CPA were associated with reduced expression of mMCP-5, but not mMCP-4, protein (FIG. 9d). mMC-CPA- or NL-shRNA-transduced BMCMCs also exhibited significantly reduced ability to degrade NT after activation with A23187 (5 μM) (FIGS. 8c and 8d). However, BMCMCs transduced with shRNAs for NLN or mMC-CPA degranulated to the same extent as empty vector-treated cells upon FcεRI cross-linking (FIG. 10), indicating that these treatments did not produce a global reduction in MC secretory function.

To assess the extent to which NLN or mMC-CPA can contribute to MC-dependent reduction of NT-induced hypotension in vivo, $Kit^{W/W-v}$ mice were engrafted with BMCMCs transduced with shRNA to silence either NLN (NLN-shRNA MCs→$Kit^{W/W-v}$) or mMC-CPA (mMC-CPA-shRNA MCs→$Kit^{W/W-v}$). Compared to results in control mice, NT induced a significant drop in MAP when administered i.p. in NLN-shRNA MCs→$Kit^{W/W-v}$ mice but not in mMC-CPA-shRNA MCs→$Kit^{W/W-v}$ mice (FIG. 8e). The percentage of PMCs among total cells in the peritoneal cavity were similar in $Kit^{W/W-v}$ mice engrafted with MCs transduced with either empty vector, NLN-shRNA or mMC-CPA-shRNA (2.8±0.1%, 3.5±0.8% or 4.0±0.9%, respectively), as were the number and distribution of MCs in the mesentery (FIG. 8f. These results indicate that MC derived-NLN is more important than mMC-CPA in protecting mice from the hypotension induced by the i.p. injection of NT in vivo.

Figure 11:
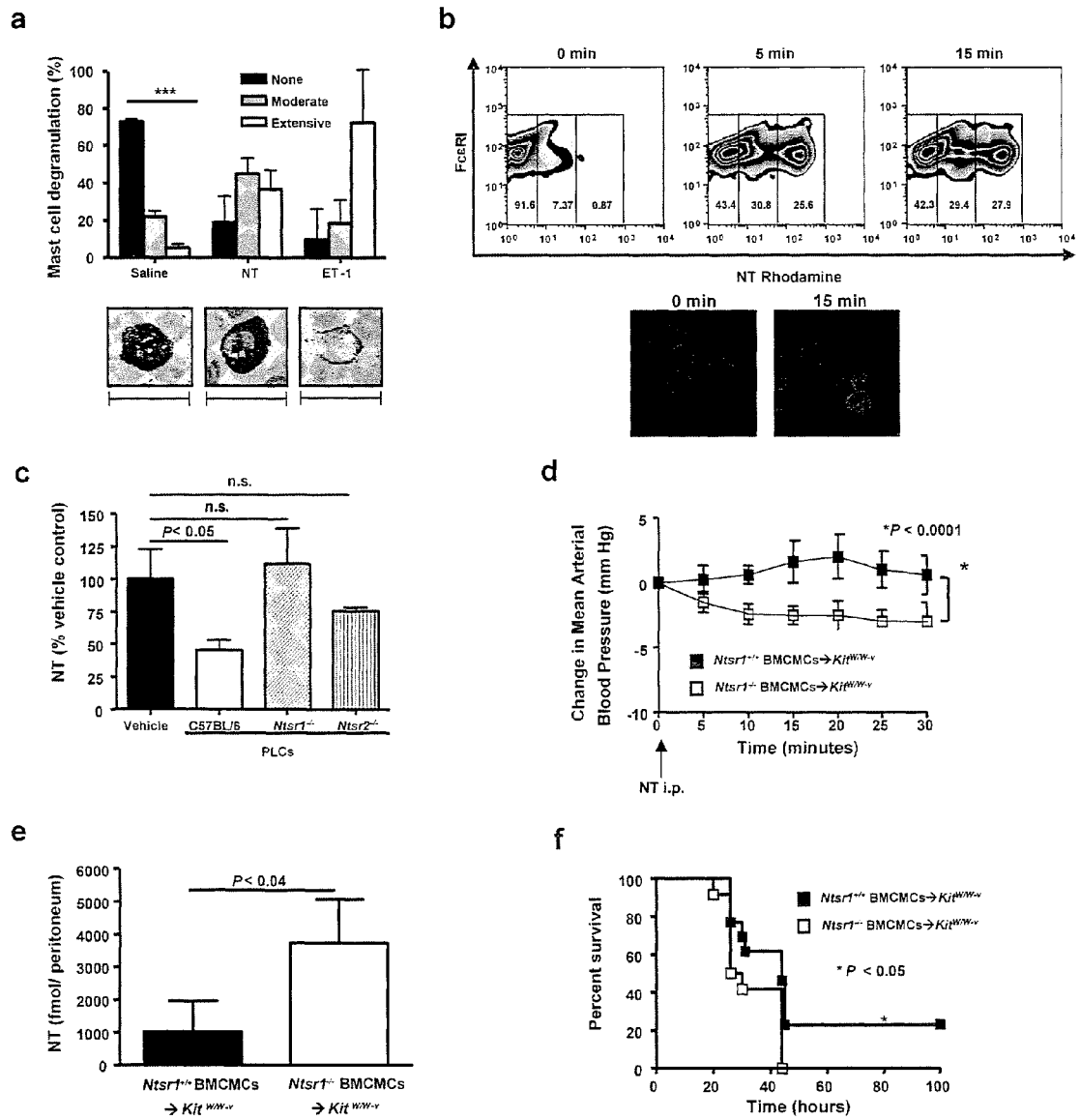
FIG. 11. MC expression of neurotensin receptor 1 (Ntsr1) reduces the hypotensive effects of NT and promotes survival in mice after CLP. (a) Percentage of PMCs obtained from Kit$^{+/+}$ mice exhibiting >50% ("Extensive"), 10-50% ("Moderate") or <10% ("None") degranulation at 30 min after injection of NT (6 nmol/300 µl saline), endothelin-1 (ET-1, 1.2 nmol/300 µl saline, used as a positive control to induce MC degranulation) or saline. P<0.0001 versus corresponding NT- or ET-1-injected groups. Photomicrographs are of May Grunwald-modified Giemsa-stained PLC preparations illustrating PMCs that exhibit no (left), moderate (middle) or extensive (right) degranulation (scale bars=10 µm). (b) Flow cytometry analysis and confocal microscopy of C57BL/6 PMCs incubated with NT-rhodamine (50 µM) (red) at 4° C. (0 min) or placed at 37° C. for 5 or 15 min. PMCs were identified among other PLCs by flow cytometry by staining of IgE bound to the MCs (green). The confocal microscope images show that staining with NT-rhodamine (red) in PMCs does not co-localize with the cell surface receptor, c-Kit (green), indicating that the some of the peptide is located within the MCs. (c) PLCs containing 5×10$^4$ PMCs from either C57BL/6, Ntsr1$^{−/−}$ or Ntsr2$^{−/−}$ mice were incubated with NT (10 µM) for 30 min at 37° C. Results are expressed as the percentage of NT remaining after incubation with cells compared to that in samples of NT incubated in vehicle alone at 37° C. (data were pooled from triplicate determinations in two independent experiments that gave similar results). (d,e) Changes in MAP vs. baseline levels (="0", measured 3 min after injection of 300 µl saline, i.p.) at various times after injection of NT (6 nmol in 300 µl saline, i.p.) (d), and NT levels in the peritoneal fluids of these mice at 30 min after injection (e), in $Kit^{W/W-v}$ mice that had been engrafted i.p. with BMCMCs of C57BL/6-$Ntsr1^{+/+}$ or -$Ntsr1^{-/-}$ origin. (f) Survival after CLP (50% ligation; single puncture with 22 G needle) in $Kit^{W/W-v}$ mice that had been engrafted i.p. with BMCMCs of C57BL/6-$Ntsr1^{+/+}$ or -$Ntsr1^{-/-}$ origin.
Figure 12:
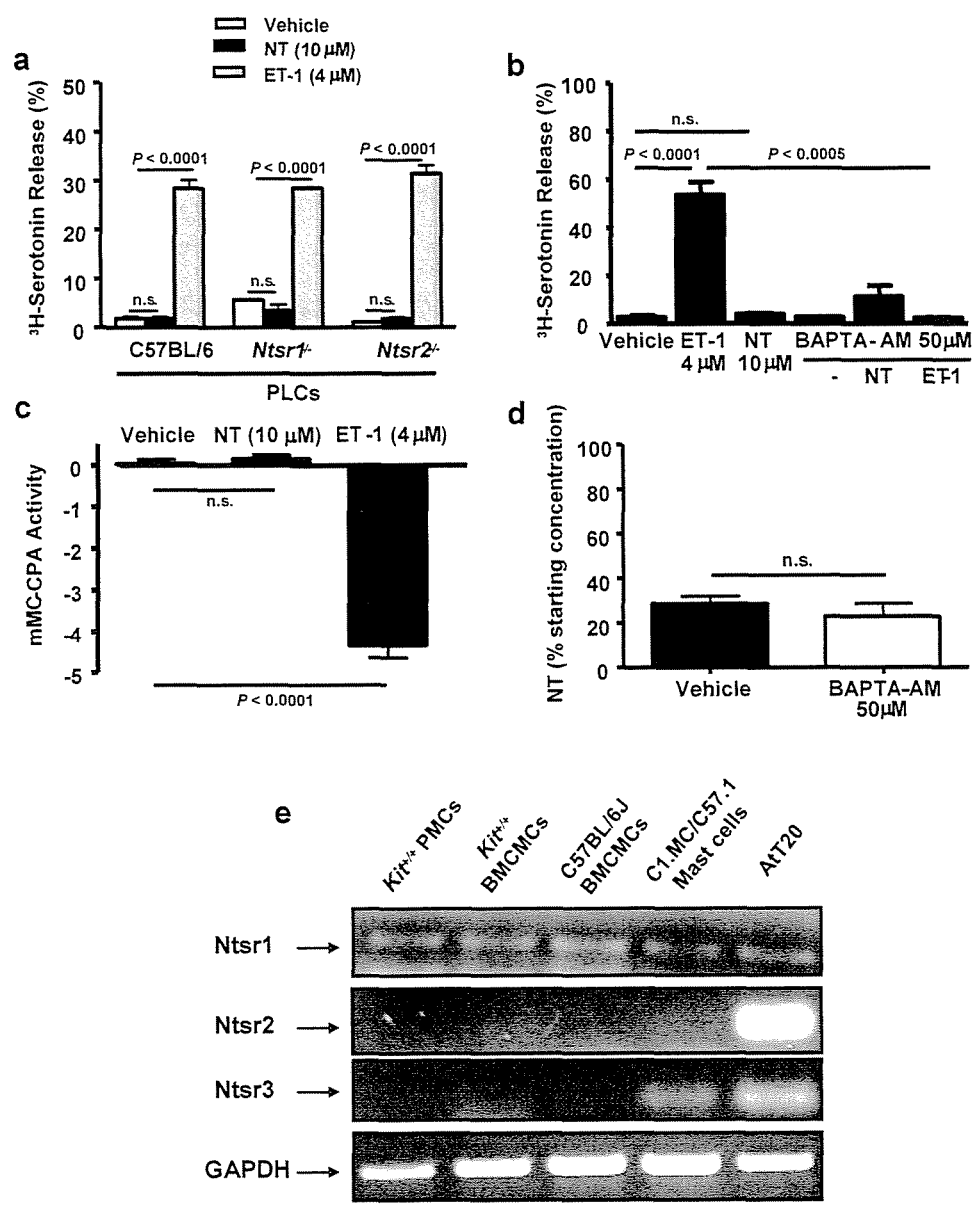
FIG. 12. (a), PLCs containing $1\times10^4$ PMCs obtained from either wild type C57BL/6 mice, Ntsr1-deficient ($Ntsr1^{-/-}$) mice or Ntsr2-deficient ($Ntsr2^{-/-}$) mice were incubated for 2 h with $^3$H-5-hydroxytryptamine (3H-serotonin) at 37° C. and stimulated for 15 min at 37° C. with either ET-1 (4 µM) or NT (10 µM). (b), PLCs containing $1\times10^4$ PMCs obtained from C57BL/6 mice were incubated for 2 h with $^3$H-serotonin and stimulated for 15 min with either ET-1 (4 µM) or NT (10 µM). In a separate set of experiments, cells were pre-incubated with BAPTA-AM (Sigma) (50 mM, 15 min at 370° C.) before the addition of the stimuli. Results are mean ±SEM of 3 experiments. (c), mMC-CPA activity was measured in supernatants obtained from $Kit^{+/+}$ PLCs containing $5\times10^4$ PMCs that were stimulated for 30 min at 37° C. with either ET-1 (4 µM) or NT (10 µM). (d), PLCs containing $5\times10^4$ PMCs from C57BL/6J mice were pre-treated for 15 min at 37° C. with BAPTA-AM (50 mM, a $Ca^{2+}$ chelator that can reduce MC degranulation) and then incubated with NT (10 µM) for 30 min at 37° C. Results are expressed as the percentage of NT remaining after incubation with cells compared to that in samples of NT incubated in vehicle alone at 37° C. (data were pooled from triplicate determinations in two independent experiments that gave similar results). (e), Expression of mRNA for NT-receptors in the AtT20 neuroendocrine cell line, the mast cell line C1.MC/C57.1, C57BL/6J BMCMCs, $Kit^{+/+}$ BMCMCs and peritoneal mast cells purified from $Kit^{+/+}$ mice (PMCs).

Notably, PMCs in $Kit^{+/+}$ mice exhibited only moderate degranulation at 30 min after i.p. injection of NT, especially when compared with PMCs in mice injected i.p. with ET-1 (FIG. 11a). Moreover, NT did not induce PMCs to release serotonin or mMC-CPA in vitro (FIGS. 12a and 12b), and inhibition of PMC degranulation with the membrane-permeable $Ca^{2+}$ chelator BAPTA-AM (50 mM, 30 min), that markedly inhibited ET-1-induced PMC serotonin release (FIG. 12c), did not reduce the ability of PMCs to degrade NT (FIG. 12d). However, by flow cytometry and confocal microscopy, we found that PMCs bound and internalized rhodamine-labelled NT (NT-rhodamine) (FIG. 11b).

There are two G protein-coupled receptors for NT, the high affinity receptor, Ntsr1, and the low affinity receptor, Ntsr2. A third binding site, Ntsr3, is a non-G protein coupled receptor of unknown function that binds NT with high affinity. NT receptors are required for optimal NT degradation, as NT degradation was significantly impaired in $Ntsr1^{-/-}$ PLCs and, to a lesser extent, in $Ntsr2^{-/-}$ PLCs (FIG. 11c). However, upon stimulation with ET-1 (4 μM), both $Ntsr1^{-/-}$- and $Ntsr2^{-/-}$-derived PMCs released serotonin to the same extent as did PMCs from the congenic wild type mice, indicating that a NT receptor-deficiency does not impair PMC degranulation in response to an agonist other than NT (FIG. 12a). These results suggest that Ntsr1 and, to a lesser extent, Ntsr2 can contribute to NT degradation by PLCs. However, we found that mouse MCs expressed Ntsr1 but not Ntsr2 (FIG. 12e), indicating that other cell types in these PLC preparations were the source of Ntsr2.

Figure 13:
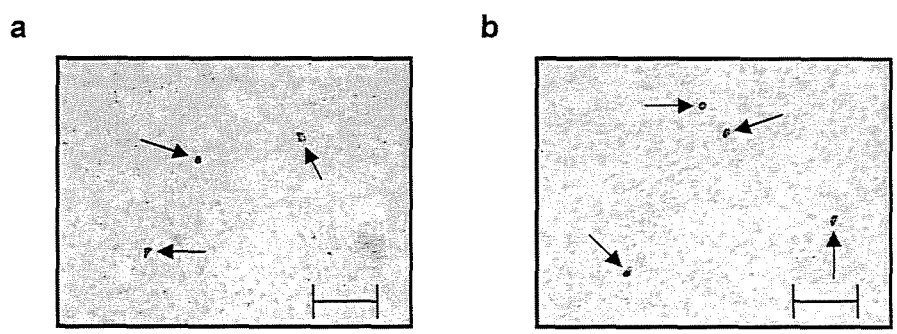
FIG. 13. MCs in the mesentery (arrows, MCs; scale bars, 100 µm; Czaba stain) of (a) $Ntsr1^{+/+}$ BMCMCs→$Kit^{W/W-v}$ or (b) $Ntsr1^{-/-}$ BMCMCs→$Kit^{W/W-v}$ mice.

We also assessed changes in MAP after i.p. injection of NT in $Kit^{W/W-v}$ mice that had been engrafted with $Ntsr1^{+/+}$ versus $Ntsr1^{-/-}$ BMCMCs. NT injection resulted in significantly lower MAP in $Ntsr1^{-/-}$ BMCMCs→$Kit^{W/W-v}$ mice than in $Ntsr1^{+/+}$ BMCMCs→$Kit^{W/W-v}$ mice (FIG. 11d), but MAP was not as low as in NT-injected $Kit^{W/W-v}$ mice (P<0.0001) (FIG. 3b). Intraperitoneal NT levels were also significantly higher in $Ntsr1^{-/-}$ BMCMCs→$Kit^{W/W-v}$ mice than in $Ntsr1^{+/+}$ BMCMCs→$Kit^{W/W-v}$ mice (FIG. 11e), but not as high as those in NT-injected $Kit^{W/W-v}$ mice (P<0.05) (FIG. 3c). Finally, survival after CLP was significantly higher in $Ntsr1^{+/+}$ BMCMCs→$Kit^{W/W-v}$ mice than in $Ntsr1^{-/-}$ BMCMCs→$Kit^{W/W-v}$ mice (23 vs. 0%, respectively, P<0.05) (FIG. 1f). The numbers of PMCs in the peritoneal cavity of $Ntsr1^{+/+}$ BMCMCs→$Kit^{W/W-v}$ or $Ntsr1^{-/-}$ BMCMCs→$Kit^{W/W-v}$ mice were very similar (3.2±0.4% or 3.8±0.8% of total cells), as were numbers of MCs in the mesentery of these mice (FIG. 13).

In summary, we show that NT is markedly elevated in the plasma of humans with sepsis and in the plasma and peritoneal cavity of mice after CLP, and that mouse MCs can degrade NT in vitro and reduce concentrations of NT in vivo, by a mechanism that involves MC expression of Ntsr1 and NLN but that may not require extensive MC degranulation. We also provide evidence that such effects of MCs on NT contribute to the ability of MCs to enhance survival after CLP. In addition to identifying MCs as regulators of NT concentrations in vivo and NT as a potential biomarker of sepsis, our findings identify neurotensin as a target for the treatment of this disorder.

Methods

Chemicals and reagents. Neurotensin (1-13) (Bachem Peninsula Labs), endothelin-1, A23187 and chymostatin (Sigma), and potato carboxypeptidase inhibitor (Calbiochem), and Pro-Ile (Bachem Peninsula Labs) were purchased from the manufacturers. Phosphodiepryl-03 and CFp-Ala-Ala-Phe-pAB were kindly provided by Dr. Vincent Dive (Commissariat a L'Ennergie Atomique, Saclay, France), and Dr. Sherwin Wilk (Mount Sinai School of Medicine, NY), respectively.

Animals. C-kit mutant genetically MC-deficient (WB/ReJ-$Kit^{W/+}$×C57BL/6J-$Kit^{W-v/+}$)$F_1$-$Kit^{W/W-v}$ (WBB6F1-$Kit^{W/W-v}$) ($Kit^{W/W-v}$) mice and the congenic normal WBB6F$_1$-+/+ ($Kit^{+/+}$) mice, and C57BL/6J mice, were purchased from Jackson Laboratories, Bar Harbor, Me. Mouse MC-protease-4 deficient ($mMCP-4^{-/-}$), NT deficient ($NT^{-/-}$), NT receptor-1 deficient ($Ntsr1^{-/-}$) and NT receptor-2 deficient ($Ntsr2^{-/-}$) mice, all on the C57BL/6 background, were bred and maintained at the Stanford University Research Animal Facility. Unless specified otherwise, all mice were 12 week old females when used for experiments. All animal care and experimentation was conducted in accord with current National Institutes of Health guidelines and with the approval of the Stanford University Institutional Animal Care and Use Committee.

Caecal ligation and puncture (CLP) CLP was performed as described by Maurer, et al. *J Exp Med.* 188: 2343-2348 (1998). Briefly, mice were deeply anesthesized by i.m. injection of 100 mg/kg Ketamine and 20 mg/kg Xylazine. The caecum was exposed by a 1-2 cm midline incision on the anterior abdomen and subjected to ligation (distal half or distal two/thirds for moderate or severe CLP, respectively) by a single puncture (22 G or 20 G for moderate or severe CLP, respectively). The caecum was then replaced into the abdomen, 1 ml of sterile saline (pyrogen-free 0.9% NaCl) was administrated into the peritoneal cavity, and the incision was closed using 9-mm steel wound clips. Mice were observed for mortality at least four times daily. Mice that were clearly moribund were killed by $CO_2$ inhalation.

Mean arterial blood pressure (MAP) measurements. Mice were anesthetized with 2%. Isoflurane. The carotid artery was exposed via a midline incision in the upper thorax and then was cannulated with a pressure transduction catheter connected to a computerized pressure monitor (Powerlab, Colorado, Springs, Colo.) to record blood pressure. The transduction system was calibrated using a sphygmomanometer. After the level of isoflurane was reduced to 1%, the blood pressure and respiratory rate of the mouse were allowed to stabilize for several minutes. Then 300 μl of saline was administered i.p. and MAP at baseline was recorded. 3 min after saline administration, NT was injected i.p. (6 nmol/300 μl saline) and blood pressure was recorded for 30 min. Data are presented as changes in MAP after NT administration in relation to baseline ("time 0").

Mast-cell engraftment of $Kit^{W/W-v}$ mice. Some $Kit^{W/W-v}$ mice (female, 4-6-week-old) were repaired of their MC deficiency selectively and locally by the i.p. injection of growth factor-dependent congenic $Kit^{+/+}$ BMCMCs. Briefly, femoral bone marrow cells from $Kit^{+/+}$ mice were maintained in vitro for ~4 weeks in IL-3-containing medium until MCs represented >95% of the total cells according to staining with May-Grünwald-Giemsa. $2.0×10^6$ BMCMCs in 200 μl of PBS, were injected i.p. (via a 26 G needle) and the mice were used for experiments, together with gender- and age-matched MC-deficient $Kit^{W/W-v}$ mice, 4-6 weeks after adoptive transfer of BMCMCs. Other $Kit^{W/W-v}$ mice received, 4-6 weeks before injection of NT i.p. or CLP, $2.0×10^6$ BMCMCs generated from either Ntsr1-deficient mice ($Ntsr1^{-/-}$) or the congenic normal mice ($Ntsr1^{+/+}$). Other $Kit^{W/W-v}$ mice received, 4 weeks before injection of NT i.p., injections of $1.0×10^6$ BMCMCs that had been transduced with NLN- or or mMC-CPA-targeting shRNA or with empty vector.

Human subjects and blood sample collection. Twelve patients presenting with severe sepsis, defined according to the criteria of the Consensus Conference of the American College of Chest Physicians and Society of Critical Care Medicine, were analyzed. Severity of disease was quantified by the Acute Physiology and Chronic Health Evaluation II (APACHE II) score. Blood samples were collected twice within 24 h of admission to the ICU. The reported NT concentrations represent the highest value measured in EDTA-plasma. Briefly, blood samples were centrifuged at 1600 g for 20 min at 4° C. Plasma was separated and stored at −80° C. Blood was obtained with the approval of the Stanford University Institutional Review Board. Blood samples from 14 healthy volunteers were provided by the Stanford Blood Center.

Lentiviral vector production. pLentiLox 3.7 (pLL3.7), a vector engineered to co-express enhanced green fluorescent protein (GFP) as a reporter gene, that permits infected cells to be tracked by flow cytometry, was digested with XhoI and HpaI and the annealed oligos (SEQ ID NO. 3) 5'-t-GAAA-CAGTTTGATGTGAAA-ttcaagaga-TTTCACATCAAACT-GTTTC-tttttc-3' and (SEQ ID NO. 4) 5'-tcgagaaaaaa-GAAACAGTTTGATGTGAAA-tctcttgaa-TTTCACATCAAACTGTTTC-a-3' for mMC-CPA and (SEQ ID NO. 5) 5'-t-GGAATGCGAAGAGCGAGGT-ttcaa-gaga-ACCTCGCTCCTTAAAATTCC-tttttc-3' (SEQ ID NO. 6) 5'-tcgagaaaaaa-GGAATGCGAAGAGCGAGGT-tctcttgaa-CTCGCTCTTCGCATTCCA-a-3' for NLN were ligated into pLL3.7 to yield a directed shRNA-producing vector. The 19 nt target sequences are indicated in capitals in the oligonucleotide sequence. Active viral stocks were created and concentrated as previously described. Briefly, 293T cells were transfected with the transfer vector plasmid pLL3.7-mMC-CPA or pLL3.7-NLN or pLL3.7 (empty vector), the VSV-G envelope-encoding plasmid pMD.G, and the packaging plasmid CMVΔR8.74 using the calcium phosphate method. The supernatants were harvested 48 or 72 h post-transfection, pooled, passed through a 0.45 µm filter, ultracentrifuged for 2 h 20 min at 19,200 rpm (66400g) in an SW28 rotor, re-suspended in 100 µl of 0.1% BSA in PBS and stored at -80° C.

Preparation of NLN- or mMC-CPA shRNA-containing MCs. 2-5 week old BMCMCs were infected with virus carrying the NLN- or mMC-CPA-targeting shRNA or the empty vector. Since pLL3.7 carries a CMV-GFP cassette, BMCMCs were sorted for GFP expression at 72-96 h after infection using FACS Aria (Becton Dickinson) and then were cultured in IMDM+10 ng/ml IL-3 (Peprotech)+10 ng/mL SCF (Amgen). $1.0 \times 10^6$ infected BMCMCs were injected i.p. into $Kit^{W/W-v}$ mice and experiments were performed 4 weeks later.

Flow cytometry and confocal microscopy. Cells were incubated for 16 h in DMEM+10% FCS+2 µg/ml IgE (hybridoma H1-DNP-ε26). Cells were washed and resuspended in DMEM+10% fetal calf serum (FCS)+NT-rhodamine (AnaSpec) (50 µM) and placed at 4° C. for 1 h. Some cells then were placed at 37° C. for 5 or 15 min. IgE Abs bound to PMCs were stained with FITC-conjugated anti-mouse IgE Abs (BD Biosciences). Levels of surface IgE were analyzed by flow cytometry, as described above.

RT-PCR, For RT-PCR, RNA (50 ng) was isolated from cells with an RNeasy mini kit (Qiagen, Valencia, CA) and converted to first-strand cDNA with oligo(dT) primers (Ambion) and Sensiscript reverse transcriptase (Qiagen) before amplification with specific primers using RETROscriptTM (Ambion). The resulting PCR products were resolved on 1.5% agarose gels. The primer pairs used for amplification were the following: (SEQ ID NO. 7) TGGGACCTCCAT-TACTACATGACC (forward) and (SEQ ID NO. 8) CCAT-AATACTGGCCGTCATACCCT (reverse) for NLN; (SEQ ID NO. 9) GCCACAGCCCTCAATGTAGCC (forward) and (SEQ ID NO. 10) GACGGTCAGTTTGTTGGCTAT (reverse) for Ntsr1; (SEQ ID NO. 11) ACAGAAGCAC-GAAATGGAGAGG (forward) and (SEQ ID no. 12) CAC-CTGGAATGTAGACCTGGAG (reverse) for Ntsr2; and (SEQ ID NO. 13) CAACAATACGCACCAGCATGTC (forward) and (SEQ ID NO. 14) CTTGGAAAGTGGTCAG-GACGAG (reverse for Ntsr3).

Membrane preparations Frozen cell pellets were resuspended in hypotonic lysis buffer (20 mM HEPES, pH 7.2, 100 mM KCl, 1 mM DTT, Complete Mini Protease Inhibitor tablets-EDTA [Roche]), lysed by sonication, and centrifuged for 5 min at 3000 rpm (960 g) to remove intact cells and nuclei. Post nuclear supernatants were centrifuged at 50000 rpm (70000 g) in a TLA55 rotor for 15 min to separate membrane from cytosol fractions.

Western blot analysis. Cells, membranes, and supernatant fractions were denatured by boiling 1 min with sample buffer (SB) (2.5% SDS 10% glycerol and 5% mercaptoethanol). Lysates were separated by SDS/PAGE, electroblotted onto Invitrolon poly(vinylidene difluoride) membranes (Invitrogen), then probed with an antibody against NLN and GAPDH (Research Diagnostics, Flanders, N.J.). Antibodies against mMCP-4 and mMCP-5 were kindly provided by Dr. Michael Gurish, Brigham and Women's Hospital and Harvard Medical School, Boston, Mass.

CPA enzymatic activity assay. CPA enzymatic activity was assessed by measuring reduction of absorbance of a chromogenic substrate (N-[4-Methoxyphenylazoformyl]-Phe-OH) (Bachem Peninsula Labs) specific for CPA as previously described.

Beta-hexosaminidase release. Beta-hexosaminidase was measured on an enzyme-linked immunosorbent assay "reader" that detects the hydrolysis product of p-nitrophenyl-N-acetyl-b-D-glucosamine (Sigma) used as a substrate.

Serotonin release. Serotonin release was assessed by the specific release, by 15 min after MC stimulation at 37° C., of [$^3$H]-hydroxytryptamine creatinine sulfate (3H-Serotonin; Perkin Elmer, Boston, Mass.) from MCs pre-loaded with $^3$H-Serotonin for 2 h at 37° C.

NT, ET-1, C-reactive protein, and TNF measurements. Concentrations of NT, C-reactive protein, ET-1 and TNF were measured by ELISA (Bachem Peninsula Labs for NT; Biomedica, Vienna for C-reactive protein and ET-1; BD Biosciences for TNF). The NT ELISA kit does not cross-react with the following NT fragments: NT (1-12), NT (1-11) and NT (1-10). The detection limits for the ELISA kits were: 24 fmol/ml (NT), 0.048 fmol/ml (ET-1), 0.124 ng/ml (C-reactive protein) and 7.8 µg/ml (human TNF).

Statistical analysis. Analysis of variance (ANOVA) for repeated measures was used to assess differences in the changes in mean arterial blood pressure. We assessed differences in the survival rates after CLP using the Mantel-Haenszel Logrank test, the extent of MC degranulation by the Chi-square test, and the association between plasma levels of biological markers and APACHE II scores by the Spearman's correlation coefficient test. All other data were analyzed for statistical significance using the unpaired two-tailed Student's t-test or Mann Whitney U-test. $P < 0.05$ is considered statistically significant. Unless otherwise specified, all data are presented as mean ±SEM.

Example 2

NT Contributes to Mortality During Severe CLP

Figure 14:
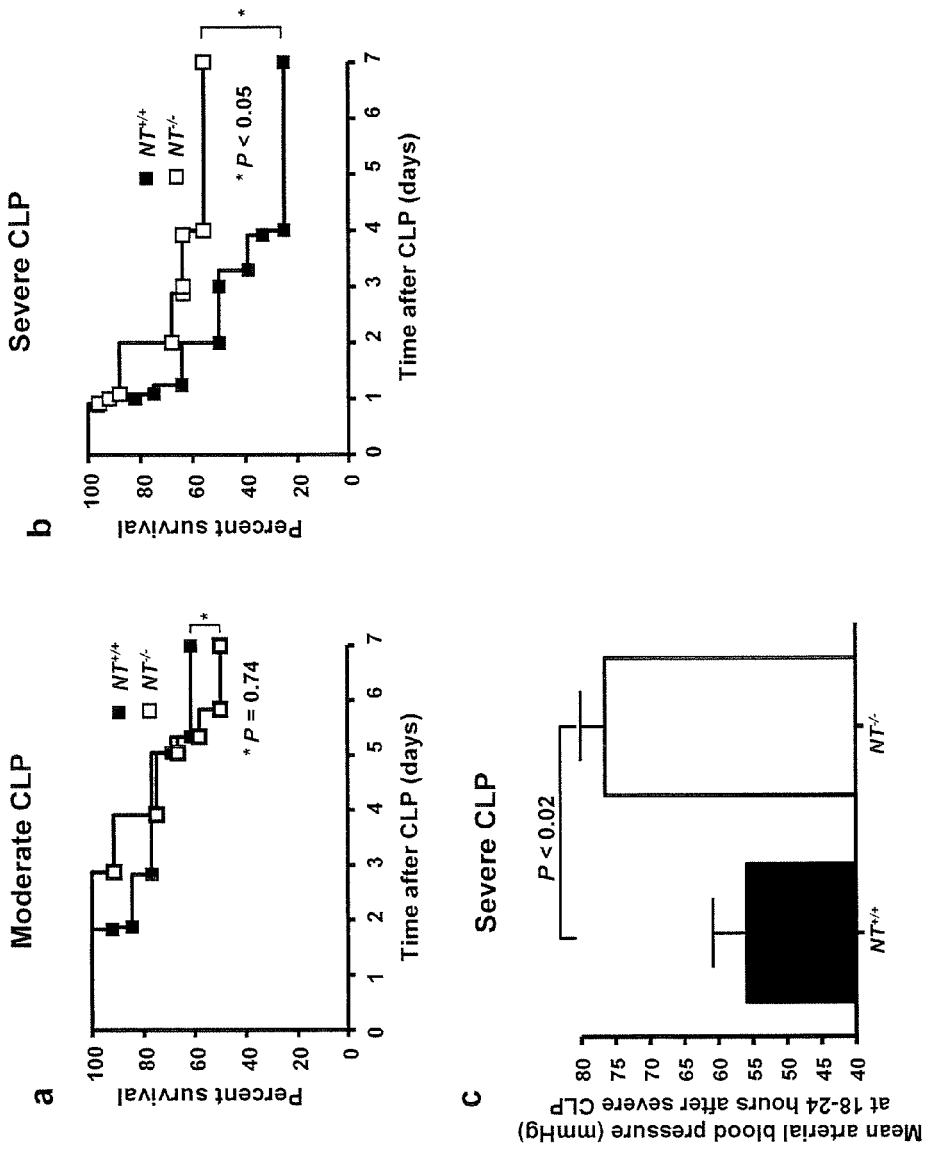
FIGS. 14a-14c (a) Survival after moderate CLP (ligation of distal half of caecum; one puncture with a 22 G needle) in 8-12-week old female and male wild type (NT+/+) (n=13) and in NT-deficient (NT−/−) (n=12) mice. (b) Survival after severe CLP (ligation of distal half of caecum; one puncture with a 20 G needle) in 8-12-week old female and male wild type (NT+/+) (n=28) and in NT-deficient (NT−/−) (n=25) mice. Data in a and b were pooled from the two or five experiments performed, respectively, each of which gave similar results. (c) Mean arterial blood pressure (MAP) in NT+/+ and NT−/− mice (n=5/group) at 18-24 hrs after severe CLP (ligation of distal half of caecum; one puncture with a 20 G needle).

A study was done comparing the importance of neurotensin (NT) in survival in moderate versus severe caecal ligation and puncture (CLP). Although the survival of wild type and NT-deficient mice was not significantly different after moderate CLP (62% vs. 50% survival for $NT^{+/+}$ and $NT^{-/-}$ mice, respectively, P<0.74) (FIG. 14a), NT$^{-/-}$ mice exhibited significantly enhanced survival after severe CLP compared to that of the littermate control (NT$^{+/+}$) mice (56% vs. 25% survival by 1 week after CLP, respectively, P<0.05) (FIG. 14b). Moreover, NT$^{+/+}$ mice exhibit lower mean arterial pressure (MAP) (55.9±4.9 mmHg) than did NT$^{-/-}$ mice (76.5±3.5 mmHg) after severe CLP (P<0.02, n=5/group) (FIG. 14c). These results indicate that NT is one of the multiple mediators responsible for the drop in systemic blood pressure (BP) observed during the severe CLP model of sepsis.

Figure 15:
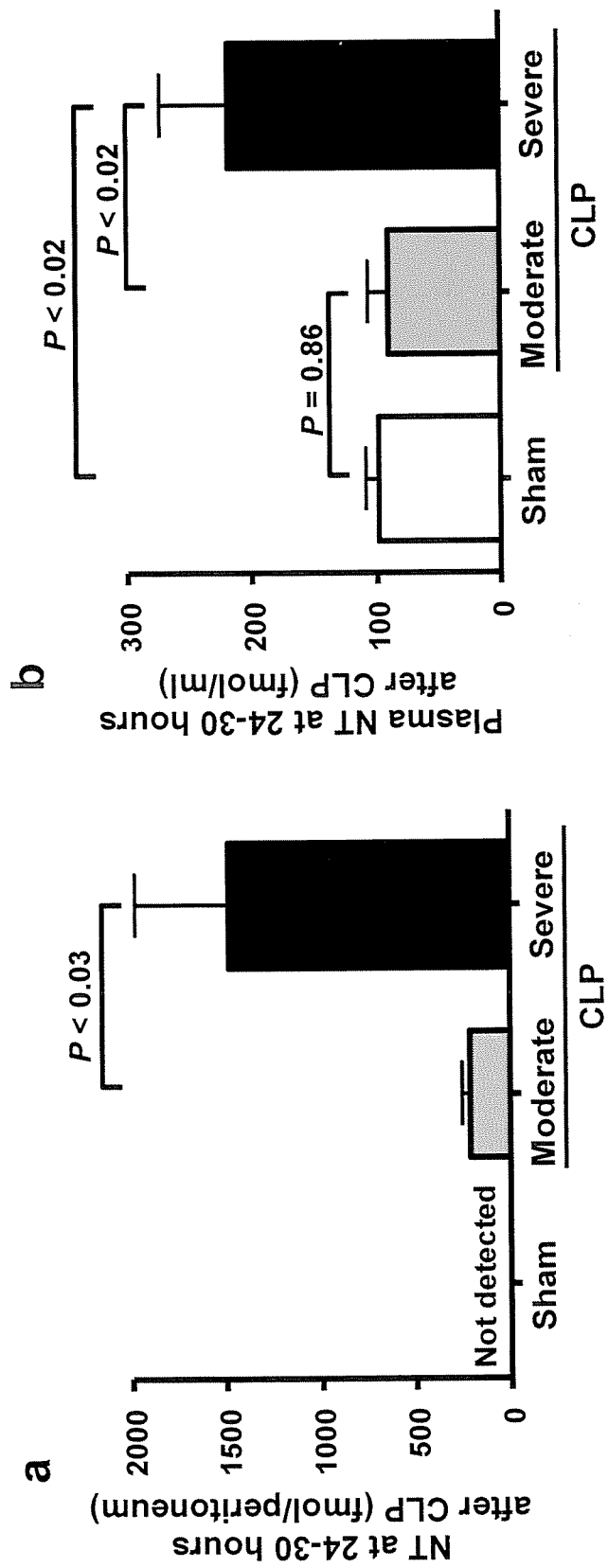
FIGS. 15a-15b (a, b) Amounts of NT in the peritoneal lavage fluid (a) and plasma concentrations of NT (b) at 24-30 h after induction of moderate CLP (ligation of distal half of caecum; one puncture with a 22 G needle) or severe CLP (ligation of the distal ⅔ of the caecum; one puncture with a 20 G needle) in 12-week old female Kit+/+ mice (n=3-9/group).

As shown in FIG. 15a, NT levels are much lower in wild type mice experiencing moderate CLP (208±48 fmol/peritoneum) than in those subjected to a model of severe CLP (1484±494 fmol/peritoneum, P<0.03). A similar finding was observed for plasma NT concentrations (90±17 fmol/ml vs. 218±55 fmol/ml, in moderate vs. severe CLP, respectively, P<0.02) (FIG. 15b). Taken together with the results presented in FIG. 1, these data demonstrate that NT has detrimental effects on survival after CLP, in those circumstances when the CLP is sufficiently severe to result in substantial elevations of NT in the peritoneal cavity and the plasma. This conclusion also is supported by the observations that levels of NT, and mortality, in moderate CLP are significantly higher in mast cell-deficient Kit$^{W/W-v}$ mice than in Kit$^{+/+}$ wild type mice (FIG. 3b).

Example 3

Figure 16:
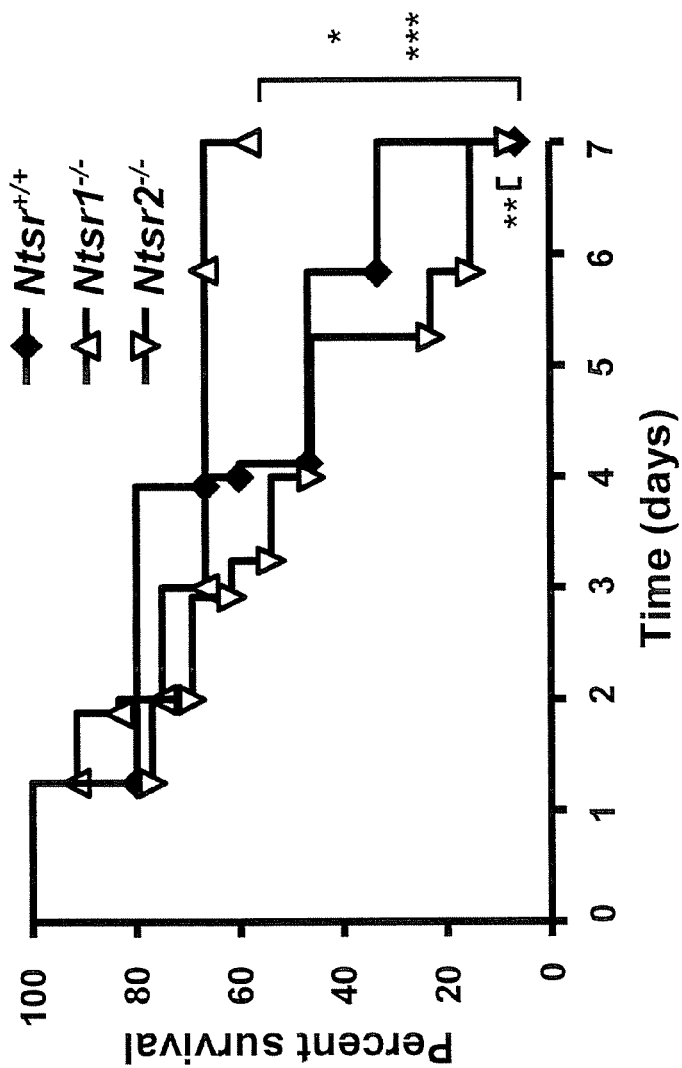
FIG. 16. Survival after severe CLP (ligation of distal half of caecum; one puncture with a 20 G needle) in 8-12-week old female and male wild type (Ntsr+/+) (n=15), Ntsr1-deficient (Ntsr−/−) (n=12) and Ntsr2-deficient (Ntsr2−/−) mice (n=13). Data were pooled from the three experiments performed, each of which gave similar results.

Expression of neurotensin receptor 1 (Ntsr1), but not neurotensin receptor 2 (Ntsr2), contributes to increased mortality after severe CLP in mice (7% vs. 58% survival for Ntsr1$^{+/+}$ vs. Ntsr1$^{-/-}$ mice, respectively, after severe CLP, P<0.03, whereas survival of Ntsr2$^{-/-}$ mice [8%] was not significantly different from that of Ntsr$^{+/+}$ mice, P=0.39) (FIG. 16). This genetic evidence strongly implicates Ntsr1 in the pathway by which increased amounts of NT can impair survival in this model of sepsis.

Figure 17:
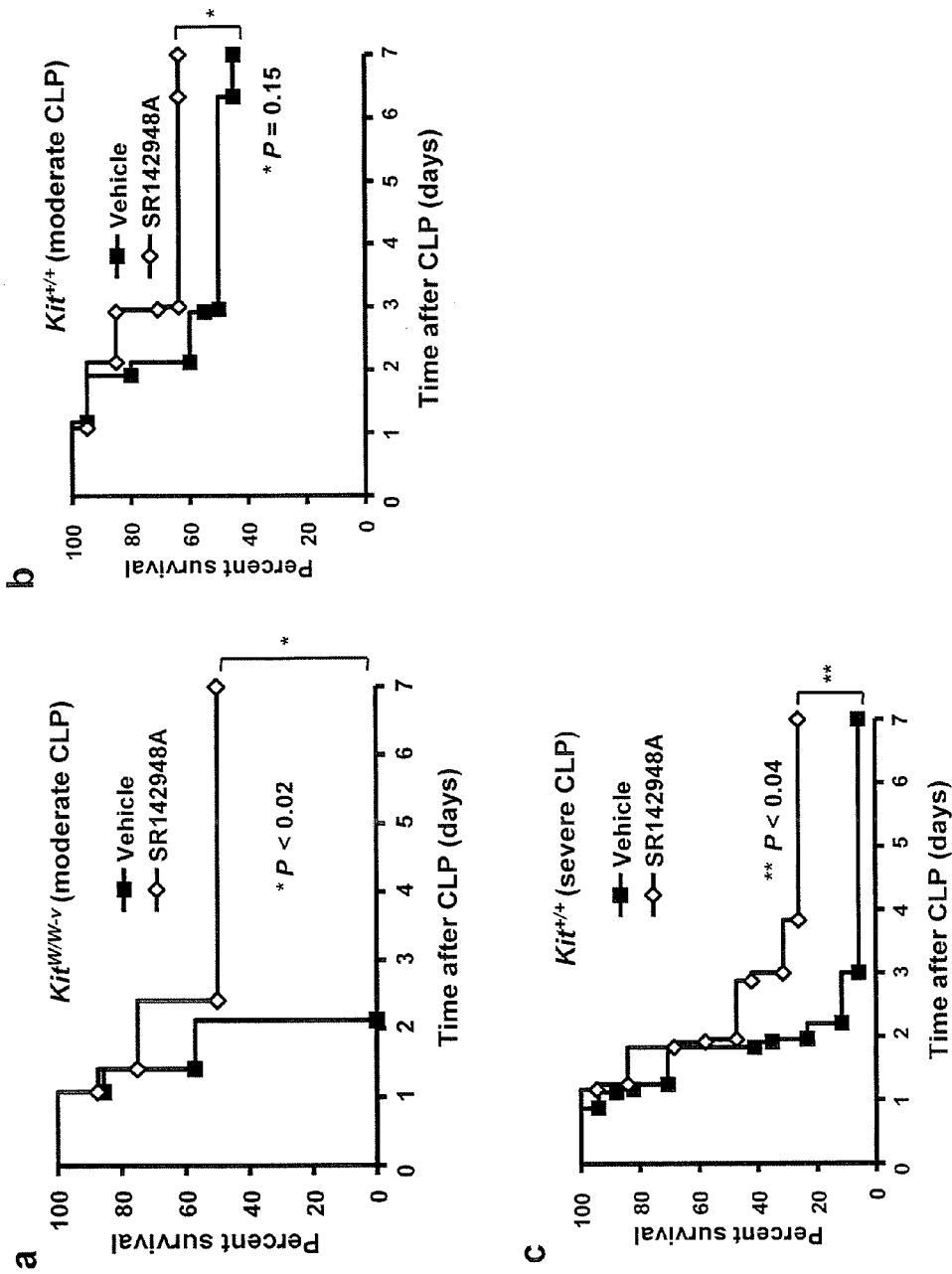
FIGS. 17a-17c. Survival in 12-week old female KitW/W-v mast cell deficient (n =7-8) (a) or wild type (Kit+/+) mice (n =20) (b) after moderate CLP. (c) Survival in 12- week old female wild type (Kit+/+) mice (n =20) after severe CLP (ligation of distal ⅔ of caecum; one puncture with a 20G needle). In a-c, mice received two i.p. injections of SR142948A (100 µg/kg in 200 µl 0.01% Tween 80 in saline [Vehicle]), or 200 µl of Vehicle, 1 h before and 8 h after CLP. Data in a-c were pooled from the three experiments performed, each of which gave similar results.

Treatment of mice subjected to moderate CLP with SR142948A (a non-selective antagonist of Ntsr1 and Ntsr2) significantly improved the survival of mast cell-deficient Kit$^{W/W-v}$ mice (FIG. 17a) but not Kit$^{+/+}$ wild type mice (FIG. 17b). This result reflects, at least in part, the higher levels of NT that developed in mast cell-deficient vs. wild type mice subjected to moderate CLP (FIG. 16b). However, in severe CLP, treatment with SR142948A also significantly improved the survival of wild type mice (FIG. 17b).

Although the evidence indicates that NT binding to peritoneal mast cell (PMC) Ntsr1 is required for optimal PMC-dependent reduction of NT levels in vitro (FIG. 11c) and for optimal effects of engrafted mast cells on the survival of mast cell-deficient mice subjected to CLP (FIG. 11f) and pharmacological blocking of Ntsr1 would impair these potentially survival-enhancing effects of adequate Ntsr1 function on mast cells, the positive consequences of pharmacological blocking of Ntsr1 (and/or Ntsr2) expression on other (non mast cell) cell types appear to be dominant in determining survival after severe CLP in this setting.

These data indicate that mast cells contribute to the survival of normal mice subjected to moderate CLP in part through the mast cell's ability to down-regulate the amounts of NT generated in this setting, thus reducing the amount of NT available to mediate pathologic effects through actions on target cells other than mast cells that express Ntsr1. However, mast cells do not deal as effectively with the larger amounts of NT generated in severe CLP.

Example 4

Mast Cells are the Only Peritoneal Cells with the Ability to Uptake and Degrade NT Among cells resident in the peritoneal cavity, mast cells are not the only source for neurolysin (NLN), a protease with NT-degrading activity. Using PCR, it was found that peritoneal cells obtained from mast cell-deficient mice also express mRNA for NLN. However, mast cells are the only peritoneal cavity cells with the ability to degrade NT under the conditions tested in in vitro experiments (FIG. 4). Moreover, the ability of mast cells to degrade NT is dependent on the cells' NLN activity (FIG. 5).

Figure 18:
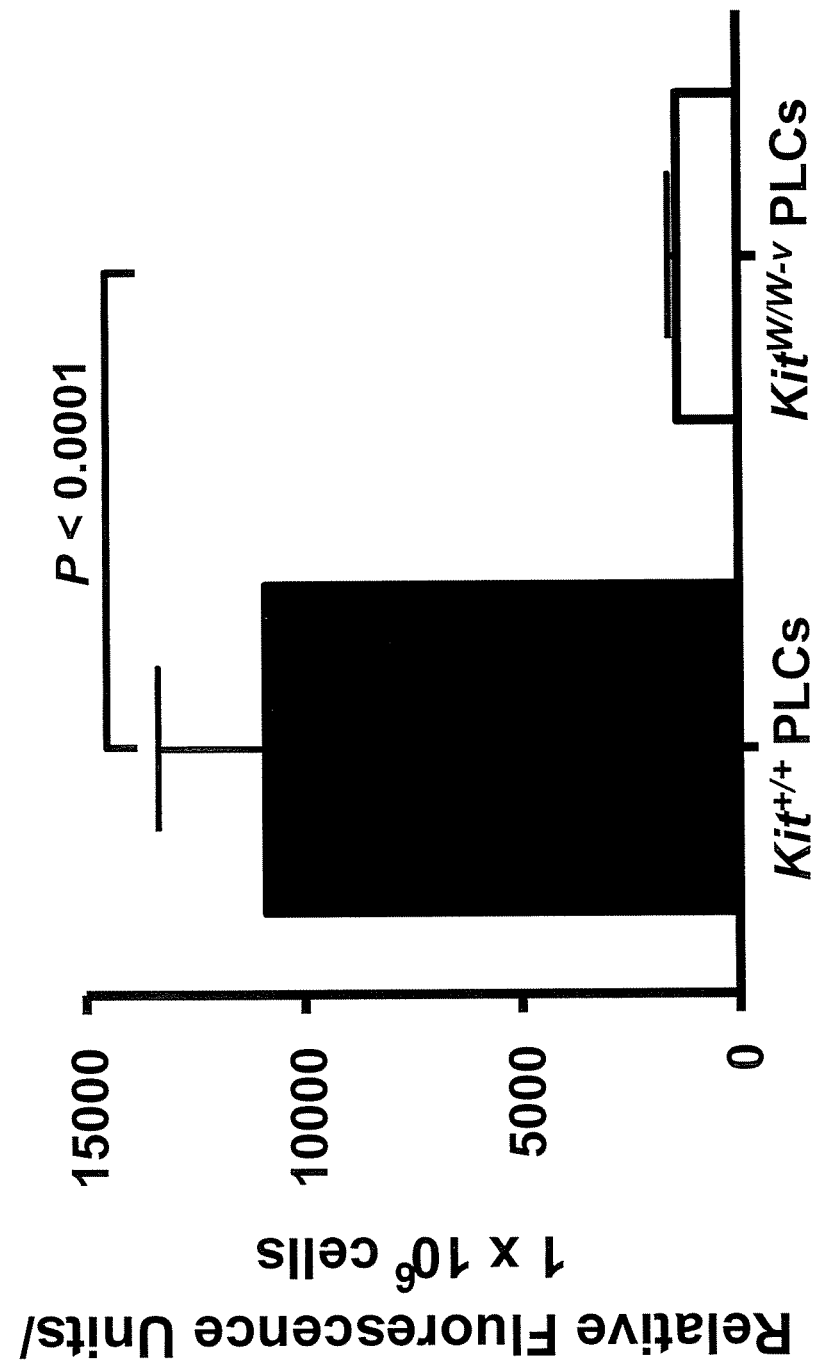
FIG. 18 Quenched Fluorescence Substrate (QFS) assay for the assessment of NLN activity in peritoneal lavage cells (PLCs) of Kit+/+mice (which contain mast cells) and KitW/W-v mice (which virtually lack mast cells). Results are expressed in relative fluorescence substrate units (RFU) generated by incubation of the quenched fluorescence substrate (QFS) for 1 h at 37 ° C. with $2\times106$ cells activated by A23187 (5 µM) (n =8 -12 replicates/group, pooled from two experiments, each of which gave similar results).

The ability of peritoneal mast cells to degrade NT better than other peritoneal cells is correlated with higher amounts of NLN activity (as assessed by a quenched fluorescence substrate [QFS] assay) in mast cells than in other cells recovered from peritoneal lavage fluid (FIG. 18).

Figure 19:
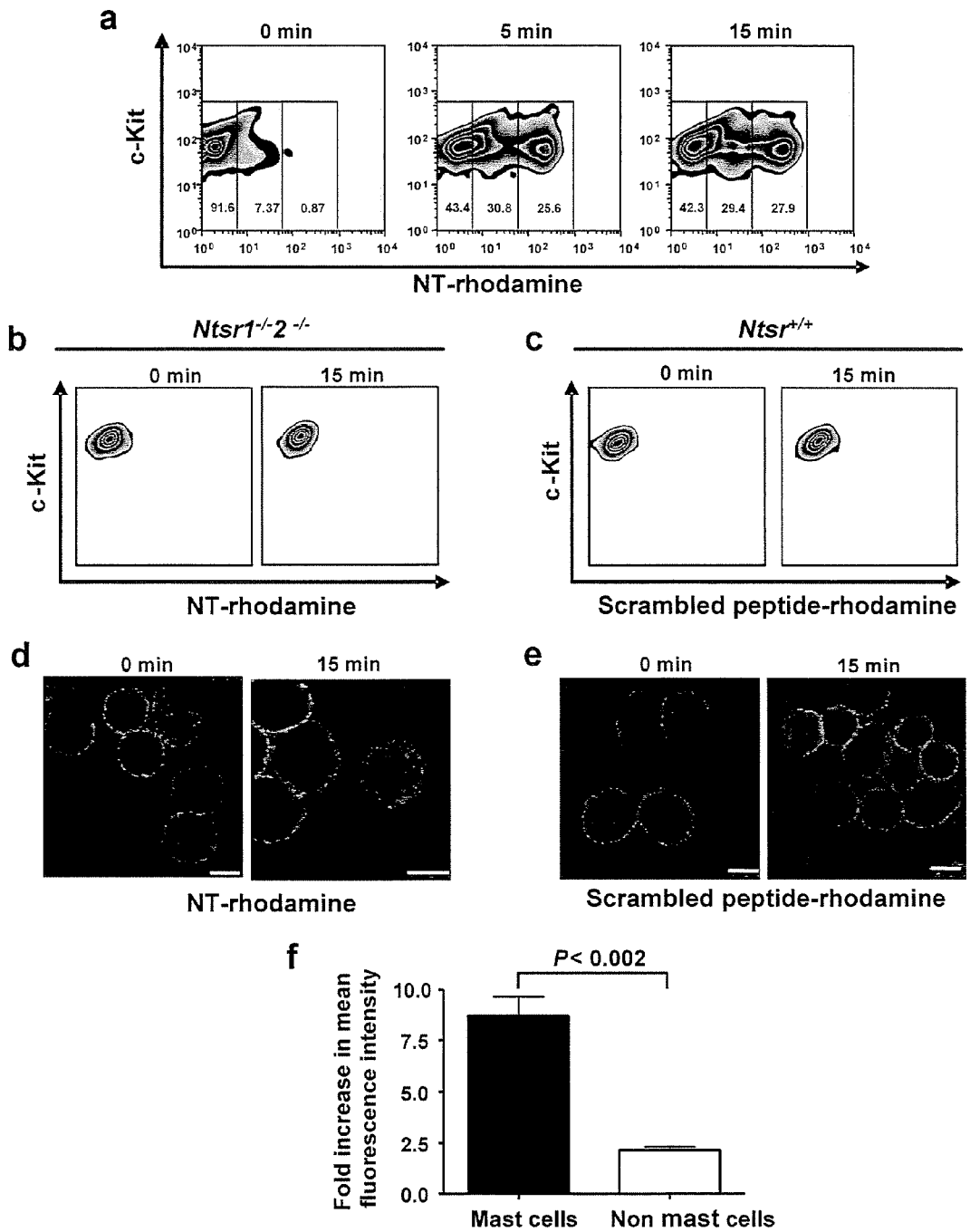
FIGS. 19a-19f. (a-c) Flow cytometry analysis and (d, e) confocal microscopy of Ntsr+/+ (a, c) or Ntsr1−/−2−/− (b) PMCs pre-loaded with either NT-rhodamine (a, b) or scrambled peptide-rhodamine (c) (10 mM) (red) that were placed at 37° C. for the indicated times. Control cells pre-loaded with either NT-rhodamine or scrambled peptide-rhodamine were maintained at 4° C. ("0 min"). PMCs were identified among other peritoneal lavage cells (PLCs) in confocal microscopy by green staining of IgE bound to the PMC surface and in flow cytometry by staining of c-Kit receptors. (f) Fold increase in mean fluorescence intensity by flow cytometry in PMCs versus other (non mast cell) PLCs obtained from Ntsr+/+ mice incubated for 15 min at 37° C. with NT-rhodamine when compared to control cells that were maintained at 4° C. for 15 min. Data are representative of (a-e) or pooled from (f) the three experiments performed, each of which gave similar results.

In addition to using the QFS assay, we analyzed the ability of mast cells and non mast cells contained among the cells in the peritoneal lavage fluid to take up NT. Using flow cytometry and confocal microscopy, we found that peritoneal mast cells (PMCs) were able to internalize rhodamine-conjugated NT (NT-rhodamine) (FIGS. 19a and 19d). By contrast, peptide internalization did not occur in PMCs that lacked expression of both Ntsr1 and Ntsr2 (FIG. 19b), nor when PMCs obtained from Ntsr$^{+/+}$ mice were incubated with a scrambled rhodamine-labeled peptide (FIGS. 19c and 19d). Taken together, these results indicate that NT internalization by mouse peritoneal mast cells depends on neurotensin receptor 1/2 expression and it is specific for NT. By using this approach, we also found that PMCs were more efficient in their ability to take up NT-rhodamine than were the non mast cells contained in the peritoneal cavity (FIG. 19f).

Example 5

Figure 20:
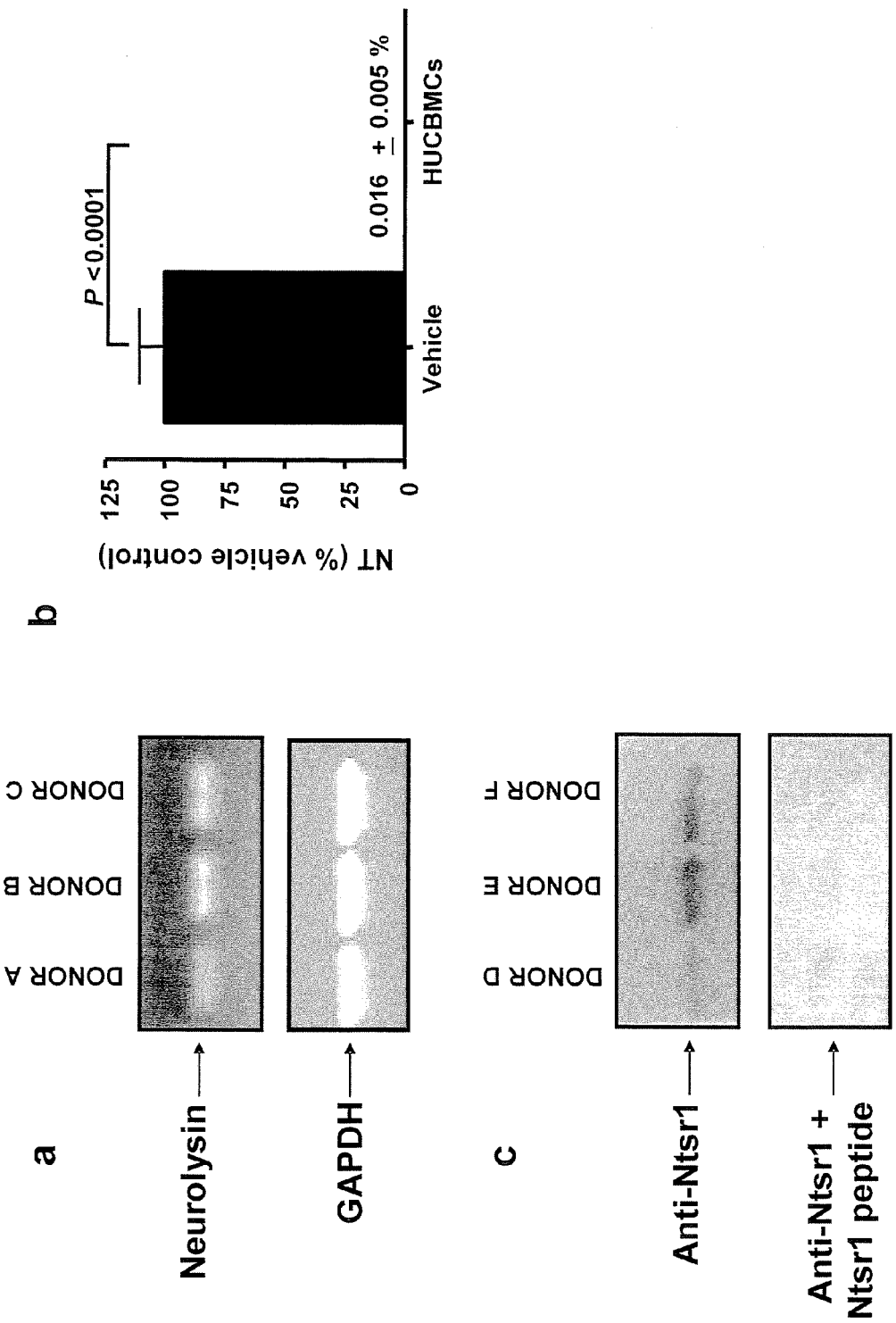
FIGS. 20a-20c. (a) Expression of mRNA for neurolysin in human umbilical cord blood-derived mast cells (HUCBMCs) obtained from three different donors. (b) Degradation of NT (10µm) by A23187 (5 µM)-activated HUCBMCs ($2\times105$). Cells were incubated with NT for 30 min at 37° C. Results are expressed as the percentage of NT remaining in the samples compared to that in samples of NT incubated in vehicle alone at 37° C. (n =3; data were pooled from the three experiments performed, each of which gave similar results). (c) Western blot analysis for Ntsr1 in lysates of HUCBMCs obtained from three different donors. Blots were incubated with Ntsr1 antiserum (anti-Ntsr1) or with Ntsr1 antiserum that had been pre-absorbed o.n. with the cognate peptide antigen (rat c-terminus of Ntsr1) (Anti-Ntsr1 +Ntsr1 peptide).

The expression of NLN mRNA was detected in human umbilical cord blood-derived mast cells (of a purity >99%) obtained from three different donors (FIG. 20a). It was also found that human umbilical cord blood-derived mast cells can degrade NT (FIG. 20b). Although human umbilical cord blood-derived mast cells express Ntsr1 (FIG. 20c), we found that NT degradation by such mast cells does not detectably occur in non-activated, "resting" mast cells, but does occur if the cells are activated by calcium ionophore (FIG. 20b). This difference between mouse peritoneal mast cells (which can degrade NT without activation by calcium ionophore) and human umbilical cord blood-derived human mast cells may reflect the fact that such in vitro-derived human mast cells are not fully mature.

What is claimed is:

1. A method for the diagnosis of sepsis, the method comprising:
determining the level of neurotensin in a blood sample from a mammalian patient suspected of having sepsis, wherein elevated levels of neurotensin relative to a normal control is indicative of sepsis.

2. The method according to claim 1, wherein said patient is a human patient.

3. The method according to claim 2, wherein said determining step comprises measuring the binding of neurotensin to a neurotensin-specific antibody.

* * * * *

SEQUENCE LISTING

<160> NUMBER OF SEQ ID NOS: 14

<210> SEQ ID NO 1

```
<211> LENGTH: 13
<212> TYPE: PRT
<213> ORGANISM: Human

<400> SEQUENCE: 1

Gln Leu Tyr Glu Asn Lys Pro Arg Arg Pro Tyr Ile Leu
 1               5                  10

<210> SEQ ID NO 2
<211> LENGTH: 170
<212> TYPE: PRT
<213> ORGANISM: Human

<400> SEQUENCE: 2

Met Met Ala Gly Met Lys Ile Gln Leu Val Cys Met Leu Leu Leu Ala
 1               5                  10                  15

Phe Ser Ser Trp Ser Leu Cys Ser Asp Ser Glu Glu Met Lys Ala
                20                  25                  30

Leu Glu Ala Asp Phe Leu Thr Asn Met His Thr Ser Lys Ile Ser Lys
                35                  40                  45

Ala His Val Pro Ser Trp Lys Met Thr Leu Leu Asn Val Cys Ser Leu
 50                  55                  60

Val Asn Asn Leu Asn Ser Pro Ala Glu Glu Thr Gly Glu Val His Glu
 65                  70                  75                  80

Glu Glu Leu Val Ala Arg Arg Lys Leu Pro Thr Ala Leu Asp Gly Phe
                85                  90                  95

Ser Leu Glu Ala Met Leu Thr Ile Tyr Gln Leu His Lys Ile Cys His
                100                 105                 110

Ser Arg Ala Phe Gln His Trp Glu Leu Ile Gln Glu Asp Ile Leu Asp
                115                 120                 125

Thr Gly Asn Asp Lys Asn Gly Lys Glu Val Ile Lys Arg Lys Ile
                130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165                 170

<210> SEQ ID NO 3
<211> LENGTH: 55
<212> TYPE: DNA
<213> ORGANISM: Artificial Sequence
<220> FEATURE:
<223> OTHER INFORMATION: Synthetic Primer

<400> SEQUENCE: 3
tgaaacagtt tgatgtgaaa ttcaagagat ttcacatcaa actgtttctt ttttc        55

<210> SEQ ID NO 4
<211> LENGTH: 59
<212> TYPE: DNA
<213> ORGANISM: Artificial Sequence
<220> FEATURE:
<223> OTHER INFORMATION: Synthetic Primer

<400> SEQUENCE: 4
tcgagaaaaa agaaacagtt tgatgtgaaa tctcttgaat ttcacatcaa actgtttca    59

<210> SEQ ID NO 5
<211> LENGTH: 56
<212> TYPE: DNA
<213> ORGANISM: Artificial Sequence
<220> FEATURE:
```

<223> OTHER INFORMATION: Synthetic Primer

<400> SEQUENCE: 5
tggaatgcga agagcgaggt ttcaagagaa cctcgctcct taaaattcct tttttc        56

<210> SEQ ID NO 6
<211> LENGTH: 58
<212> TYPE: DNA
<213> ORGANISM: Artificial Sequence
<220> FEATURE:
<223> OTHER INFORMATION: Synthetic Primer

<400> SEQUENCE: 6
tcgagaaaaa aggaatgcga agagcgaggt tctcttgaac tcgctcttcg cattccaa      58

<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
tgggacctcc attactacat gacc        24

<210> SEQ ID NO 8
<211> LENGTH: 24
<212> TYPE: DNA
<213> ORGANISM: Artificial Sequence
<220> FEATURE:
<223> OTHER INFORMATION: Synthetic Primer

<400> SEQUENCE: 8
ccataatact ggccgtcata ccct        24

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
gccacagccc tcaatgtagc c        21

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
gacggtcagt tgttggcta t        21

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
acagaagcac gaaatggaga gg        22

<210> SEQ ID NO 12

```
-continued

<211> LENGTH: 22
<212> TYPE: DNA
<213> ORGANISM: Artificial Sequence
<220> FEATURE:
<223> OTHER INFORMATION: Synthetic Primer

<400> SEQUENCE: 12
cacctggaat gtagacctgg ag                                              22

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
caacaatacg caccagcatg tc                                              22

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer

<400> SEQUENCE: 14
cttggaaagt ggtcaggacg ag                                              22
```